(12) United States Patent
Williams et al.

(10) Patent No.: US 11,878,087 B2
(45) Date of Patent: *Jan. 23, 2024

(54) ORIENTED IMPLANTS CONTAINING POLY(BUTYLENE SUCCINATE) AND COPOLYMER, AND METHODS OF USE THEREOF

(71) Applicant: Tepha, Inc., Lexington, MA (US)

(72) Inventors: Simon F. Williams, Cambridge, MA (US); Said Rizk, Windham, NH (US); David P. Martin, Arlington, MA (US)

(73) Assignee: Tepha, Inc., Lexington, MA (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/290,727

(22) Filed: Mar. 1, 2019

(65) Prior Publication Data

US 2019/0269816 A1 Sep. 5, 2019

Related U.S. Application Data

(60) Provisional application No. 62/733,384, filed on Sep. 19, 2018, provisional application No. 62/636,930, filed on Mar. 1, 2018.

(51) Int. Cl.
*A61L 27/18* (2006.01)
*A61F 2/00* (2006.01)
(Continued)

(52) U.S. Cl.
CPC .......... *A61L 27/18* (2013.01); *A61F 2/0045* (2013.01); *A61F 2/0063* (2013.01); *A61F 2/12* (2013.01);
(Continued)

(58) Field of Classification Search
None
See application file for complete search history.

(56) References Cited

U.S. PATENT DOCUMENTS

| 5,349,028 A | 9/1994 | Takahashi |
| 7,317,069 B2 | 1/2008 | Aoshima |

(Continued)

FOREIGN PATENT DOCUMENTS

| CN | 105903073 | 8/2016 |
| CN | 106957434 | 7/2017 |

(Continued)

OTHER PUBLICATIONS

Food and Drug Administration's Guidance for Industry Pyrogen and Endotoxins Testing: Questions and Answers (Jun. 2012) acessed online on Feb. 11, 2021 at https://www.fda.gov. (Year: 2012).*

(Continued)

*Primary Examiner* — Carlos A Azpuru
*Assistant Examiner* — Casey S Hagopian
(74) *Attorney, Agent, or Firm* — Wolf, Greenfield & Sacks, P.C.

(57) ABSTRACT

Resorbable implants comprising poly(butylene succinate) and copolymers thereof have been developed. The implants implants are preferably sterilized, and contain less than 20 endotoxin units per device as determined by the limulus amebocyte lysate (LAL) assay, and are particularly suitable for use in procedures where prolonged strength retention is necessary, and can include one or more bioactive agents. The implants may be made from fibers and meshes of poly (butylene succinate) and copolymers thereof, or by 3d printing, and the fibers may be oriented. Coverings and receptacles made from forms of poly(butylene succinate) and copolymers thereof have also been developed for use with cardiac rhythm management devices and other implantable devices. These coverings and receptacles may be used to hold, or partially/fully cover, devices such as pacemakers and neurostimulators. The coverings and receptacles are made from meshes, webs, lattices, non-wovens, films, fibers, (Continued)

and foams, and contain antibiotics such as rifampin and minocycline.

30 Claims, 3 Drawing Sheets

(51) Int. Cl.
*A61F 2/12* (2006.01)
*A61L 17/10* (2006.01)
*A61L 27/56* (2006.01)
*A61L 27/58* (2006.01)
*A61L 31/06* (2006.01)
*A61L 31/14* (2006.01)
*A61L 17/12* (2006.01)
*A61L 27/54* (2006.01)
*A61L 17/06* (2006.01)
*A61L 27/48* (2006.01)
*A61L 31/16* (2006.01)
*A61L 17/00* (2006.01)
*D02G 3/04* (2006.01)
*D02G 3/44* (2006.01)
*C08L 65/00* (2006.01)
*C08L 67/00* (2006.01)

(52) U.S. Cl.
CPC .......... *A61L 17/06* (2013.01); *A61L 17/105* (2013.01); *A61L 17/12* (2013.01); *A61L 27/54* (2013.01); *A61L 27/56* (2013.01); *A61L 27/58* (2013.01); *A61L 31/06* (2013.01); *A61L 31/146* (2013.01); *A61L 31/148* (2013.01); *C08L 65/00* (2013.01); *C08L 67/00* (2013.01); *D02G 3/045* (2013.01); *D02G 3/448* (2013.01); *D02G 3/449* (2013.01); *A61F 2002/0068* (2013.01); *A61F 2220/0016* (2013.01); *A61F 2240/002* (2013.01); *A61F 2250/0067* (2013.01); *A61L 17/005* (2013.01); *A61L 27/48* (2013.01); *A61L 31/16* (2013.01); *A61L 2300/404* (2013.01); *A61L 2300/416* (2013.01); *A61L 2430/04* (2013.01); *A61L 2430/34* (2013.01); *A61L 2430/38* (2013.01); *D10B 2331/04* (2013.01); *D10B 2401/063* (2013.01); *D10B 2509/04* (2013.01)

(56) References Cited

U.S. PATENT DOCUMENTS

| | | | |
|---|---|---|---|
| 7,700,500 | B2 | 4/2010 | Jordan |
| 7,972,692 | B2 | 7/2011 | Chakravarty |
| 8,680,229 | B2 | 3/2014 | Maeda |
| 8,747,974 | B2 | 6/2014 | Nakano |
| 10,058,639 | B2* | 8/2018 | Zhang ............ A61L 31/08 |
| 10,595,983 | B1* | 3/2020 | Ferguson ............ A61F 2/08 |
| 10,689,498 | B2 | 6/2020 | Connelly et al. |
| 10,994,057 | B2* | 5/2021 | Williams ............ A61L 27/20 |
| 11,292,885 | B1 | 4/2022 | Connelly et al. |
| 2008/0147165 | A1 | 6/2008 | Hossainy |
| 2009/0171037 | A1 | 7/2009 | Aoshima |
| 2010/0249332 | A1 | 9/2010 | Ferguson |
| 2010/0249361 | A1* | 9/2010 | Wang ............ C08G 63/60 528/84 |
| 2011/0293685 | A1 | 12/2011 | Kuo et al. |
| 2012/0283826 | A1 | 11/2012 | Moses |
| 2013/0090521 | A1 | 4/2013 | Lau |
| 2013/0267972 | A1 | 10/2013 | Peniston et al. |
| 2014/0276995 | A1 | 9/2014 | Lau |
| 2015/0148514 | A1* | 5/2015 | Makal ............ C08G 18/08 528/85 |
| 2015/0258238 | A1 | 9/2015 | Ferguson |
| 2019/0269815 | A1 | 9/2019 | Williams et al. |
| 2019/0269816 | A1 | 9/2019 | Williams |
| 2019/0269817 | A1 | 9/2019 | Williams et al. |
| 2019/0269822 | A1 | 9/2019 | Williams et al. |
| 2020/0390933 | A1 | 12/2020 | Williams et al. |
| 2020/0390944 | A1 | 12/2020 | Williams et al. |
| 2021/0046212 | A1 | 2/2021 | Williams et al. |
| 2021/0047484 | A1 | 2/2021 | Williams et al. |
| 2021/0244860 | A1 | 8/2021 | Williams et al. |
| 2022/0202988 | A1 | 6/2022 | Williams et al. |

FOREIGN PATENT DOCUMENTS

| | | | |
|---|---|---|---|
| IN | 201641013616 | | 4/2016 |
| JP | 7-11517 | A | 1/1995 |
| JP | 07-173715 | A | 7/1995 |
| JP | 08-134719 | A | 5/1996 |
| JP | 08-158154 | A | 6/1996 |
| JP | 09-41220 | A | 2/1997 |
| JP | 09-195122 | A | 7/1997 |
| JP | 10-99424 | A | 4/1998 |
| JP | 2000-282357 | A | 10/2000 |
| JP | 2007-215803 | A | 8/2007 |
| JP | 2007-222277 | A | 9/2007 |
| JP | 2013-042914 | A | 3/2013 |
| JP | 2016124935 | | 7/2016 |
| WO | WO 2006/115226 | A1 | 11/2006 |
| WO | 2014173055 | | 10/2014 |
| WO | 2016192632 | | 12/2016 |

OTHER PUBLICATIONS

Ojansivu et al. "Knitted 3D Scaffolds of Polybutylene Succinate Support Human Mesenchymal Stem Cell Growth and Osteogenesis", Stem Cells International, vol. 2018, Article ID 5928935, 11 pages, May 2018. (Year: 2018).*
Polybutylene succinate, polymer properties database. accessed online on Feb. 12, 2021 at https://polymerdatabase.com (Year: 2021).*
Definition of "mastopexy". Accessed online on Feb. 10, 2021 at https://www.plasticsurgery.org. (Year: 2021).*
Definition of "rhytidectomy". Accessed online on Feb. 10, 2021 at https://www.plasticsurgery.org. (Year: 2021).*
Definition of "orient". Accessed online on Feb. 10, 2021 at https://www.collinsdictionary.com. (Year: 2021).*
Costa-Pinto, et al., "Chitosan-poly(butylene succinate) scaffolds and human bone marrow stromal cells induce bone repair in a mouse calvaria model", J. of Tissue Eng. and Regen. Med., 6:21-28 (2012).
De Geyter, et al., "Non-Thermal Plasma Surface Modification of Biodegradable polymers", Biomedical Science, Engineering and Technology, 10:225-248 (2012).
International Search Report for PCT/US2019/020348 dated Jul. 3, 2019.
International Search Report for PCT/US2020/048773 dated Dec. 10, 2020.
Manavitehrani, et al., "Biomedical Applications of Biodegradable Polyesters", Polymers, 8:20-52 (2016).
Wang, et al., "Biocompatibility and bioactivity of plasma-treated biodegradable poly (butylene succinate)", Acta Biomaterialia, 5(1):279-287 (2009).
Gigli, et al., "Poly(butylene succinate)-based polyesters for biomedical applications: A review", Eur. Polym. J., 75:431-60 (2016).
Kun, et al., Biocompatibility of a novel poly(butyl succinate) and polylactic acid blend ASAIO Journal,, 58:262-7 (2012).
Li, et al., "n vitro evaluation of biodegradable poly(butylene succinate) as a novel biomaterial", Macromol. Biosci., 5:433-40 (2005).
Vandesteene, et al., "Synthesis of Branched Poly(butylene succinate): Structure Properties Relationship", Chin. J. Polym. Sci., 34(7):873-88 (2016).
Xu and Guo, "Poly(butylene succinate) and its copolymers: research, development and industrialization", Biotechnol. J. 5:1149-63 (2010).
Jacquel, et al., "Synthesis and Properties of Poly(butylene succinate): Efficiency of Different Transesterification Catalysts", Journal of Polymer Science, Part A: Polymer Chemistry, 48:5301-5312, (2011).

(56) References Cited

OTHER PUBLICATIONS

Ribeiro, et al., "Evaluation of Novel 3D Architectures Based on Knitting Technologies for Engineering Biological Tissues", International Conference on Medical Textiles and Healthcare Products, MedTex13, Raleigh, NC, USA (2013).
Office Action for Australian Application No. 2019226562, dated Apr. 8, 2022 and claims as pending as of Apr. 8, 2022.
Office Action for Canadian Application No. 3,091,812, dated Oct. 6, 2021 and claims as pending as of Oct. 6, 2021.
Office Action for Japanese Application No. 2020-545319 dated Jan. 6, 2022 and machine translation of claims as pending as of Jan. 6, 2022.
Office Action for Japanese Application No. 2020-545319 dated Aug. 22, 2022 and machine translation of claims as pending as of Aug. 22, 2022.
International Preliminary Report on Patentability for PCT/US2020/048773 dated Nov. 12, 2021.

* cited by examiner

ORIENTED IMPLANTS CONTAINING POLY(BUTYLENE SUCCINATE) AND COPOLYMER, AND METHODS OF USE THEREOF

CROSS-REFERENCE TO RELATED APPLICATIONS

This application claims the benefit of and priority to U.S. Application No. 62/636,930, filed Mar. 1, 2018 and U.S. Application No. 62/733,384, filed on Sep. 19, 2018, which is hereby incorporated herein by reference in their entirety.

FIELD OF THE INVENTION

The present invention generally relates to oriented implants made from resorbable polymeric compositions and methods of use thereof. The devices contain poly(butylene succinate) and copolymers thereof.

BACKGROUND OF THE INVENTION

Multifilament products made from resorbable polymers, such as copolymers of glycolide and lactide, and monofilament products made from resorbable polymers, such as polydioxanone (PDO), are well known in the prior art, and widely used in wound closure and general surgery. However, these products undergo rapid loss of strength retention in vivo, which limits their application primarily to fast healing repairs, and repairs where prolonged strength retention is not necessary. For example, while a surgeon may use a resorbable multifilament suture to approximate soft tissue that is not under significant tension, a surgeon will generally not use a resorbable suture when loads on the suture can be very high and remain high for a prolonged period, such as in rotator cuff repairs. Instead, surgeons will typically use permanent sutures for rotator cuff repairs even though it would be desirable to use a suture that is completely resorbed once healing is complete. Similarly, a surgeon may use a resorbable monofilament suture or mesh to approximate soft tissue that is not under significant tension, but will generally not use a resorbable monofilament suture or mesh when loads on the device can be very high and remain high for a prolonged period, such as in hernia repair. Instead, surgeons will typically use permanent (polypropylene) meshes for hernia repairs even though it would be desirable to use devices that completely resorb after healing is complete.

Recently, an aliphatic polyester, poly(butylene succinate) (PBS) has been commercialized for use in industrial applications such as paper coatings, packaging, and mulch films (U.S. Pat. No. 7,317,069 to Aoshima, U.S. Pat. No. 8,680, 229 to Maeda, U.S. Pat. No. 8,747,974 to Nakano, WO2014173055A1 to Xu, and US Patent Application 20100249332 to Ferguson.). The industrial polymer is produced through condensation polymerization from readily available starting materials, succinic acid and 1,4-butanediol. Xu and Guo, *Biotechnol. J.* 5:1149-1163 (2010) have reviewed the industrialization of the PBS polymer, Li et al. have evaluated poly(butylene succinate) in vitro (Li et al. *Macromol. Biosci.* 5:433-440 (2005)), Vandesteene et al. *Chin. J. Polym. Sci.*, 34(7):873-888 (2016) have studied the structure-property relationships of the polymer. Kun et al. *ASAIO Journal*, 58:262-267 (2012) have studied the biocompatibility of blends of PBS with polylactic acid, and Gigli et al. *Eur. Polym. J.*, 75:431-460 (2016) have reviewed the polymer's in vitro biocompatibility. However, no FDA-approved implants containing poly(butylene succinate) or copolymers thereof have been successfully developed.

One reason that progress in developing implants made from PBS and copolymers thereof has been prevented is that the mechanical properties of the polymers were unsatisfactory, particularly when compared to alternative medical grade polymers. Low molecular weights of PBS and copolymers thereof were mainly responsible for the poor mechanical properties. In order to increase molecular weight, new methods of polymer synthesis have more recently been successfully developed, and industrial products made from PBS and copolymers thereof have now been introduced. These advances in improving molecular weight relied upon the use of isocyanate chemistry to increase the molecular weight of PBS, and provide polymers with good mechanical properties (U.S. Pat. No. 5,349,028). Unfortunately, this approach is not a good option for the development of biocompatible degradable implants due to the toxicity associated with isocyanate chemistry.

In the practice of surgery there currently exists a need for resorbable fibers with high tensile strength and prolonged strength retention. These fibers, including multifilament yarns and monofilament fibers, would allow the surgeon to use resorbable devices instead of permanent devices when high strength is initially required, or when prolonged strength retention is necessary. For example, monofilament resorbable fibers with high strength and prolonged strength retention could be used to make monofilament surgical meshes suitable for hernia repair, breast reconstruction and mastopexy, treatment of stress urinary incontinence, and pelvic floor reconstruction. And multifilament yarns with high tenacity and prolonged strength retention could be used, for example, in the repair of the rotator cuff and other ligaments and tendons, as well as for hernia repair or breast lift procedures. Other processing techniques, such as 3D printing, including fused filament fabrication, could also be used to make implants with prolonged strength retention, including lattices and other porous constructs, suitable for use in, for example, hernia repair, breast reconstruction and mastopexy, treatment of stress urinary incontinence, and pelvic floor reconstruction.

There is thus a need to develop resorbable implants with prolonged strength retention and preferably high initial tensile strength that also have good biocompatibility, can be produced economically, and degrade to non-toxic degradation products.

It is an object of the present invention to provide biocompatible implants of poly(butylene succinate) and copolymers thereof with prolonged strength retention.

It is a further object of the present invention to provide implants of poly(butylene succinate) and copolymers thereof that are made from oriented fibers, including monofilament and multifilament fibers.

It is yet a further object of the present invention to provide implants of poly(butylene succinate) and copolymers thereof that are made by 3D printing.

It is another object of the present invention to provide processes to produce oriented implants and 3D printed implants of poly(butylene succinate) and copolymers thereof.

It is still another object of the invention to provide methods for implantation of implants made from poly(butylene succinate) and copolymers thereof.

SUMMARY OF THE INVENTION

Resorbable biocompatible implants comprising poly (butylene succinate) and copolymers thereof have been developed. These implants are made using poly(butylene succinate), copolymers, or blends thereof, and are produced so that the implants are biocompatible, contain less than 20 endotoxin units per device as determined by the limulus amebocyte lysate (LAL) assay, and are sterile. The poly (butylene succinate) polymer comprises succinic acid and 1,4-butanediol, two compounds that are converted by hydrolysis to natural metabolites in vivo, and which degrade by known metabolic/catabolic pathways to carbon dioxide and water without the formation of toxic metabolites. The poly (butylene succinate) and copolymers thereof are also made without the use of croslinking agents that can result in toxic metabolites being released from the implants as the polymers degrade. The implants are particularly suitable for use in procedures where prolonged strength retention is necessary, such as hernia repair, breast reconstruction and augmentation, mastopexy, orthopedic repairs, wound management, pelvic floor reconstruction, treatment of stress urinary incontinence, stenting, heart valve surgeries, dental procedures and other plastic surgeries. The preparation of the implants avoids the use of production technologies that produce endotoxin, or require the use of antibiotics. Preferably, the implants are made from polymeric compositions of poly(butylene succinate) and copolymers thereof, wherein the melting temperatures of the compositions are between 105° and 120° C., and thus the implants are stable during transportation in hot climates as well as in storage. The polymeric compositions used to prepare the implants preferably exclude the use of poly(butylene succinate) and copolymers thereof that have been prepared with the use of isocyanates. In a preferred embodiment, the implants comprise polymeric compositions comprising 1,4-butanediol and succinic acid units copolymerized with one or more hydroxycarboxylic acid units, even more preferably wherein the hydroxycarboxylic acid units are malic acid, citric acid, or tartaric acid. In a particularly preferred embodiment, the implants comprise succinic acid-1,4-butanediol-malic acid copolyester. In another embodiment, the implants comprise polymeric compositions comprising 1,4-butanediol and succinic acid units copolymerized with maleic acid, fumaric acid, or combinations thereof. These polymeric compositions may further comprise other monomers, including malic acid, citric acid or tartaric acid.

In an embodiment, the implants are made from fibers and meshes comprising poly(butylene succinate) and copolymers thereof. In a preferred embodiment, the fibers are oriented. The fibers in certain embodiments are monoaxially or biaxially oriented. It has been discovered that the oriented fibers do not curl when uneven forces are applied to their surfaces during implantation. For example, these fibers do not curl, or form pig tail structures, when used as sutures and tension is applied unevenly to the suture's surfaces. Pig tailing of suture fibers is undesirable because it makes the handling of surgical sutures very difficult during implantation. It has also been discovered that oriented fibers of poly(butylene succinate) and copolymers thereof can be prepared that are not pitted during degradation after implantation in vivo. This fiber property provides a predictable degradation profile in vivo and is particularly important for the performance of small diameter fibers and multifilament fibers. Pitting of the surface of a small diameter fiber, or uneven erosion of the fiber surface, can result in the premature loss of strength retention of the fiber leading to early failure of the fiber in vivo. Premature loss of strength retention results from the effective cross-section of the fiber being decreased by pitting. The absence of pitting of the fibers is particularly important in all fiber-based implants, and especially important in implants where prolonged strength retention is desirable like sutures, surgical meshes, hernia meshes, breast reconstruction meshes, mastopexy meshes, and slings. Pitting can be visualized using SEM as indents, micropores or hollowing of the surface of the fiber.

In one embodiment, oriented monofilament and multifilament fibers of poly(butylene succinate) and copolymers, which may be monoaxially or biaxially oriented, have been developed with very high tensile strengths, but that still degrade in vivo over time. It has been discovered that these fibers can be prepared using multi-stage orientation in combination with heated conductive liquid chambers. The high tensile strengths of these fibers make them suitable for use in resorbable implant applications requiring high tensile strength and prolonged strength retention. Such applications include hernia repair, breast reconstruction, treatment of urinary incontinence with slings, suturing, mesh suturing, and ligament and tendon repair. In another embodiment, it has been discovered that this new method of fiber formation can also be used to prepare oriented monofilament and multifilament fibers of poly(butylene succinate) and copolymers that are relatively stiff with Young's Modulus values between 2 and 3 GPa. The high stiffness of these fibers is particularly advantageous in the preparation, handling, and performance of resorbable implantable sutures and surgical meshes. It has also been found that the poly(butylene succinate) and copolymer compositions can be used to prepare orthopedic implants with sufficient stiffness and torsional strengths to make them useful in resorbable implants such as interference screws and suture anchors. It has also been discovered that surgical meshes can be prepared from poly(butylene succinate) and copolymers thereof that are dimensionally stable when implanted in vivo, and do not shrink for at least 4 weeks, or at least 12 weeks, following implantation, i.e., the width and length of the mesh do not decrease in size substantially, or significantly. In Table 8 shows that the relative area of the mesh does not shrink. The width and length remain relatively constant. Whereas data for the GalaFLEX mesh is given in Table 9, and the area of the mesh and dimensions decrease. Accordingly, in this embodiment, the area of the mesh decreases by less than 6, for example, less than 5%, less than 4%, less than 2% and less than 1% by 12 weeks compared to its initial area, and the area of the mesh decreases by less than 4%, preferably, less than 2% and even more preferably between 0% and 1% at 4 weeks post implantation, compared to its initial area.

The surgical meshes are prepared from oriented fibers of poly(butylene succinate) and copolymers thereof. In certain embodiments, the fibers are monoaxially or biaxially oriented. The improved meshes prevent additional tension being placed on tissues at the implant site, and maintain the original area of reinforcement or repair. Furthermore, it has also been discovered that the meshes do not curl along their edges after implantation, and continue to contour to the patient's anatomy. Curling of implantable mesh along its edges is undesirable because it can expose neighboring tissue to mesh edges and result in tissue damage.

In a further embodiment, the implants are made by 3D printing compositions comprising poly(butylene succinate) and copolymers thereof. In a particularly preferred embodiment, the implants made by 3D printing have porous structures, and even more preferably lattice structures. It has been discovered that certain compositions of poly(butylene succinate) and copolymers thereof can be 3D printed to produce implants where surprisingly the printed polymers have a higher weight average molecular weight than the compositions from which they are derived.

In another embodiment, the implants contain one or more antimicrobial agents to prevent colonization of the implants, and reduce or prevent the occurrence of infection following implantation in a patient. Coverings and receptacles made from forms of poly(butylene succinate) and copolymers thereof have also been developed for use with cardiac rhythm management devices and other implantable devices. These coverings and receptacles may be used to hold, or partially or fully cover, devices such as pacemakers, breast implants, and neurostimulators. In a preferred embodiment, the coverings and receptacles are made from meshes, nonwovens, films, fibers, foams, 3D printed objects, and contain antibiotics such as rifampin and minocycline. The implants comprising poly(butylene succinate) and copolymers thereof can be sterilized by irradiation, but are more preferably sterilized by ethylene oxide gas or cold ethylene oxide gas.

DETAILED DESCRIPTION OF THE INVENTION

Figure 1:
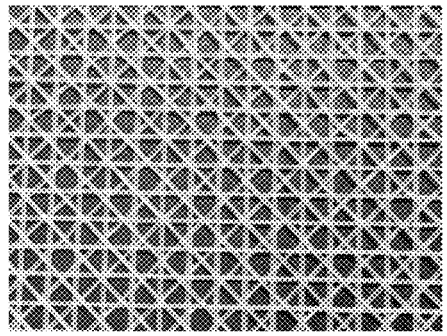
FIG. 1 is an image showing a 3D printed mesh produced by melt extrusion deposition (MED) of succinic acid-1,4-butanediol-malic acid copolyester.

Methods have been developed to prepare resorbable implants with prolonged strength retention that contain poly(butylene succinate) or copolymer thereof. These implants preferably have high initial strength, and contain less than 20 endotoxin units per device as determined by the limulus amebocyte lysate (LAL) assay. After implantation, the implants degrade slowly providing sufficient time for healing before the strength of the implant is lost. In certain embodiments, the implants are in the form of scaffolds which allow tissue ingrowth to occur over a prolonged period of time on account of the prolonged strength retention. The implants may contain one or more antimicrobial agents to prevent colonization of the implants, and reduce or prevent the occurrence of infection following implantation in a patient. After implantation, the implants are designed to release the antimicrobial agents. The implants may also be coated on one or more surfaces to prevent adhesions forming to the coated surfaces. In one embodiment, the implants may be delivered minimally invasively, and the implants may also be three-dimensional with or without the ability to resume their original shapes after being deformed for delivery. The implants are particularly suitable for use in procedures where prolonged strength retention is required, such as hernia repair, including abdominal, ventral, incisional, umbilical, inguinal, femoral, hiatal and paraesophageal hernia, breast reconstruction and augmentation, mastopexy, orthopedic repairs including ligament and tendon repair, wound management, suturing, pelvic floor reconstruction, treatment of stress urinary incontinence, stenting, heart valve surgeries, dental procedures and other plastic surgeries. In one preferred embodiment, methods have been developed to produce implants with highly oriented fibers and meshes of poly(butylene succinate) and copolymers thereof. Maintenance of the high degree of orientation of these fibers and meshes is essential to their physical function in vivo. The high degree of orientation of the fibers and meshes allows these devices to retain strength in the body for prolonged periods ("prolonged strength retention"), and therefore provide critical support to tissues during reconstruction and repair procedures. If orientation is lost during preparation of the implants containing these fibers and meshes, the resulting products will have lower strength and strength retention, and be unable to provide the necessary reinforcement and configuration required for healing. For example, spray coating or dip coating of oriented poly (butylene succinate) fibers using many solvents results in loss of fiber orientation and loss of strength retention. Methods have been developed that allow fibers and meshes of poly(butylene succinate) and copolymers thereof to be prepared without substantial loss of orientation of the fibers, and therefore without substantial loss of strength and strength retention. Optionally, these implants may also incorporate other bioactive agents, such as antibiotics, antimicrobials, and anti-adhesion agents.

In another preferred embodiment, methods have been developed to produce implants of poly(butylene succinate) and copolymers by 3D printing, including free deposition modeling, including fused filament fabrication, fused pellet deposition, and melt extrusion deposition, selective laser melting, and solution printing. A particularly preferred 3D printing method is fused filament fabrication. In a preferred embodiment, the implants comprising poly(butylene succinate) and copolymers produced by 3D printing are porous, and in a particularly preferred embodiment the implants may be lattices, including meshes containing struts or fibers.

Methods have also been developed to prepare resorbable enclosures, pouches, holders, covers, meshes, non-wovens, films, clamshells, casings, and other receptacles made from poly(butylene succinate) and copolymers thereof that partially or fully encase, surround or hold implantable medical devices, and optionally wherein the poly(butylene succinate) and copolymers thereof contain and release one or more antimicrobial agents to prevent colonization of the implants and/or reduce or prevent infection. Implantable medical devices that can be partially or fully encased include cardiac rhythm management (CRM) devices (including pacemakers, defibrillators, and generators), implantable access systems, neurostimulators, ventricular access devices, infusion pumps, devices for delivery of medication and hydration solutions, intrathecal delivery systems, pain pumps, breast implants, and other devices to provide drugs or electrical stimulation to a body part.

In one embodiment, the methods disclosed herein are based upon the discovery that oriented implants and 3D printed implants of poly(butylene succinate) and copolymers thereof retain their strength longer than copolymers of glycolide and lactide, and monofilament products made from polydioxanone (PDO). The oriented and 3D printed implants of poly(butylene succinate) and copolymers thereof can also be prepared with high initial strength.

Methods have also been developed to prepare resorbable implants comprising poly(butylene succinate) and copolymers thereof that may be used for soft and hard tissue repair, regeneration, and replacement. In some embodiments, the polymeric composition is monoaxially or biaxially oriented. These implants include, but not limited to: suture, barbed suture, braided suture, monofilament suture, hybrid suture of monofilament and multifilament fibers, braids, ligatures, knitted or woven meshes, knitted tubes, catheters, monofilament meshes, multifilament meshes, patches, pultruded profiles, laminates, wound healing device, bandage, wound dressing, burn dressing, ulcer dressing, skin substitute, hemostat, tracheal reconstruction device, organ salvage device, dural substitute, dural patch, nerve guide, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, injectable particles, injectable microspheres, bulking or filling device, bone marrow scaffold, clip, clamp, screw, pin, nail, medullary cavity nail, bone plate, interference screw, tack, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including but not limited to atrial septal defect repair devices and PFO (patent foramen *ovale*) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, and device for facial scar revision. In a particularly preferred embodiment, these implants comprise polymeric compositions comprising 1,4-butanediol and succinic acid units copolymerized with one or more hydroxycarboxylic acid units, even more preferably wherein the hydroxycarboxylic acid units are malic acid, citric acid, or tartaric acid. In a particularly preferred embodiment, these implants comprise succinic acid-1,4-butanediol-malic acid copolyester. In another embodiment, the implants comprise polymeric compositions comprising 1,4-butanediol and succinic acid units copolymerized with maleic acid, fumaric acid, or combinations thereof. These polymeric compositions may further comprise other monomers, including malic acid, citric acid or tartaric acid.

I. Definitions

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, antimicrobials, antibiotics, antiparasitic agents, sugars, polysaccharides, nucleotides, oligonucleotides, hyaluronic acid and derivatives thereof, aptamers, siRNA, nucleic acids, and combinations thereof. "Bioactive agent" includes a single such agent and is also intended to include a plurality.

"Biocompatible" as generally used herein means the biological response to the material or device being appropriate for the device's intended application in vivo. Any metabolites or degradation products of these materials should also be biocompatible.

"Blend" as generally used herein means a physical combination of different polymers, as opposed to a copolymer comprised of two or more different monomers.

"Burst strength" as used herein unless otherwise stated is determined by test method based on ASTM D6797-02 "Standard test method for bursting strength of fabrics constant rate of extension (CRE) ball burst test," using a MTS Q-Test Elite universal testing machine or similar device. However, the testing fixture uses a ⅜ inch diameter ball and the opening is ½ inch diameter.

"Copolymers of poly(butylene succinate)" as generally used herein means any polymer of succinic acid and butylene monomers incorporating one or more additional monomers. Examples of copolymers of poly(butylene succinate) include poly(butylene succinate-co-adipate), poly(butylene succinate-co-terephthalate), poly(butylene succinate-co-ethylene succinate), and poly(butylene succinate-co-propylene succinate). Poly(butylene succinate-co-adipate), for example, may be made by condensation polymerization from succinic acid, adipic acid and 1,4-butanediol. Copolymers of poly(butylene succinate) include polymers comprising (i) succinic acid and 1,4-butanediol units, and (ii) one or more of the following additional units, such as: chain extenders, cross-linking agents, and branching agents. Examples of these copolymers include: succinic acid-1,4-butanediol-malic acid copolyester, succinic acid-1,4-butanediol-citric acid copolyester, succinic acid-1,4-butanediol-tartaric acid copolyester, succinic acid-1,4-butanediol-malic acid copolyester further comprising citric acid, tartaric acid, or a combination thereof, succinic acid-adipic acid-1,4-butanediol-malic acid copolyester, succinic acid-adipic acid-1,4-butanediol-citric acid copolyester, succinic acid-adipic acid-1,4-butanediol-tartaric acid copolyester, or succinic acid-adipic acid-1,4-butanediol-malic acid copolyester further comprising citric acid, tartaric acid, or combinations thereof. Copolymers of poly(butylene succinate) also include polymers comprising succinic acid and 1,4-butanediol units and one or more hydroxycarboxylic acid unit. The copolymers may also comprise maleic or fumaric acid units, or combinations thereof.

"Diameter" as generally used herein is determined according to the US Pharmacopeia (USP) standard for diameter of surgical sutures (USP 861).

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Endotoxin content" as used herein refers to the amount of endotoxin present in a sample, and is determined by the limulus amebocyte lysate (LAL) assay.

"Mesh suture" as used herein means a device including a needle and a mesh component that can be used to re-appose soft tissue. The mesh suture is designed to be threaded through soft tissue, and the mesh component anchored under tension to re-appose soft tissue. The mesh component helps to prevent the suture from cutting through the tissues (suture pullout or cheese-wiring), and increases the strength of the repair, when compared to conventional monofilament and multifilament sutures.

"Molecular weight" as used herein, unless otherwise specified, refers to the weight average molecular weight (Mw), not number average molecular weight (Mn), and is measured by gel permeation chromatography (GPC) relative to polystyrene standards.

"Orientation ratio" as used herein is the ratio of the output speed to the input speed of two godets (or rollers) used to orient the multifilament yarn or monofilament fiber. For example, the orientation ratio would be 3 if the output speed of the multifilament yarn or monofilament fiber is 6 meters per minute, and the input speed of the multifilament yarn or monofilament fiber is 2 meters per minute.

"Phosphate buffered saline" as used herein is prepared by diluting a 10× Phosphate Buffered Saline, Ultra Pure Grade (Product #J373-4L, from VWR) to 1× with deionized water and adding 0.05 wt % sodium azide (NaN3, Product # 14314 from Alfa Aesar) as a biocide. The resulting 1× buffer solution contains 137 mM NaCl, 2.7 mM KCl, 9.8 mM phosphate and 0.05 wt % sodium azide and has pH 7.4 at 25° C. The prepared solution is filtered through a 0.45 μm filter (VWR Product # 10040-470) prior to use.

"Poly(butylene succinate)" as generally used herein means an aliphatic polyester containing succinic acid and 1,4-butanediol units, and may be made by condensation polymerization from succinic acid and 1,4-butanediol. Poly(butylene succinate) may be abbreviated as "PBS". Poly(butylene succinate) includes polymers of (i) succinic acid and 1,4-butanediol units, and (ii) one or more additional monomers, including the following: chain extenders, cross-linking agents, and branching agents.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Strength retention" refers to the amount of time that a material maintains a particular mechanical property following implantation into a human or animal. For example, if the tensile strength of a resorbable fiber decreased by half over 3 months when implanted into an animal, the fiber's strength retention at 3 months would be 50%.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Taber Stiffness Unit" is defined as the bending moment of ⅕ of a gram applied to a 1½" (3.81 cm) wide specimen at a 5-centimeter test length, flexing it to an angle of 15°, and is measured using a Taber V-5 Stiffness Tester Model 150-B or 150-E. The TABER® V-5 Stiffness Tester-Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 0.0981 milliNewton meters (mN m). Taber Stiffness Units can be converted to Genuine Gurley™ Stiffness Units with the equation: $S_T=0.01419S_G-0.935$, where $S_T$ is the stiffness in Taber Stiffness Units and $S_G$ is the stiffness in Gurley Stiffness Units. To convert Taber Stiffness Units to milliNewton Meters, use the equation: $X=S_T \cdot 0.098067$, where X is the stiffness in milliNewton Meters. When explants do not meet the size requirements for the Taber test due to limitations in the available testing sizes for implantation in an experimental animal, the values may be used to determine changes in the relative stiffness or provide comparative values between samples of the same size.

"Tenacity" means the strength of a yarn or a filament for its given size, and is measured as the grams of breaking force per denier unit of yarn or filament and expressed as grams per denier (gpd).

"Tensile modulus" is the ratio of stress to strain for a given material within its proportional limit.

"Tensile strength" as used herein means the maximum stress that a material can withstand while being stretched or pulled before failing or breaking.

"Yarn" as used herein means a continuous strand of textile fibers, or filaments. The yarn may be twisted, not twisted, or substantially parallel strands.

II. Compositions

Methods have been developed to produce resorbable implants comprising poly(butylene succinate) and copolymers thereof. The resorbable implants may be used for soft and hard tissue repair, regeneration, and replacement.

In one embodiment, the implants comprise fibers with prolonged strength retention. The fibers may be monofilament or multifilament fibers, and are preferably oriented. The fibers preferably have an in vivo strength retention of at least 70% at 4 weeks, and more preferably at least 80% or 90% strength retention at 4 weeks. The fibers preferably have an in vivo strength retention of at least 50% at 12 weeks, and more preferably at least 65% strength retention at 12 weeks. These properties make the fibers suitable for use in implants requiring prolonged strength retention, such as hernia meshes, breast reconstruction meshes, sutures, slings for treatment of stress urinary incontinence, mesh sutures, and pelvic floor reconstruction devices. In addition to having prolonged strength retention, these fibers preferably have one or more of the following properties: (i) tensile strengths greater than 400 MPa, 500 MPa, 600 MPa, 700 MPa, or 800 MPa, but less than 2,000 Pa, and more preferably between 400 MPa and 1,200 MPa, (ii) Young's Modulus greater than 600 MPa, 700 MPa, 800 MPa, 900 MPa, 1 GPa, or 2 GPa, but less than 3GPa, and (iii) elongation to break of 10-150%, more preferably 10-50%.

Methods have also been developed to produce implants comprising PBS or copolymer thereof that can partially or fully encase, surround or hold implantable medical devices, and wherein the PBS or copolymers thereof release one or more antimicrobial agents to prevent colonization of the implantable medical devices and/or reduce or prevent infection in the patient. Suitable implants comprising PBS or copolymers thereof include pouches, holders, covers, meshes, non-wovens, lattices, webs, films, clamshells, casings, and receptacles.

In another embodiment, methods are described to prepare implants comprising PBS and copolymers thereof that are relatively stiff. In one embodiment, the polymeric compositions of PBS and copolymers thereof can be used to prepare orthopedic implants. These implants have sufficient stiffness and torsional strength to make them suitable for use in resorbable implants such as interference screws, suture anchors, bone anchors, clips, clamps, screws, pins, nails, medullary cavity nails, bone plates, interference screw, tacks, fasteners, rivets, staples, fixation devices for an implant, and bone void fillers.

Methods to process PBS and copolymers thereof by 3D printing into resorbable implants are also described. The methods are particularly suitable for making meshes, void fillers, lattices, tissue scaffolds and complex 3D shapes for use as implants.

A. Poly(butylene succinate) and Copolymers

The methods described herein can typically be used to produce resorbable implants and resorbable enclosures, pouches, holders, covers, meshes, non-wovens, webs, lattices, films, clamshells, casings, and other receptacles from poly(butylene succinate) and copolymers thereof. Copolymers contain other diols and diacids in addition to the 1,4-butanediol and succinate monomers, and may alternatively or additionally contain branching agents, coupling agents, cross-linking agents and chain extenders. Examples of diols and diacids that can be included are: 1,3-propanediol, ethylene glycol, 1,5-pentanediol, glutaric acid, adipic acid, terephthalic acid, malonic acid, and oxalic acid. The copolymers may contain one or more additional diols and diacids in addition to 1,4-butanediol and succinic acid. Copolymers include, but are not limited to, poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate).

The resorbable implants described herein may be produced from poly(butylene succinate) and copolymers thereof wherein the polymer or copolymer has been produced using one or more of the following: chain extenders or coupling agents, cross-linking agents, and branching agents. For example, poly(butylene succinate) or copolymer thereof may be branched or cross-linked by adding one or more of the following agents: malic acid, trimethylol propane, trimesic acid, citric acid, glycerol propoxylate, and tartaric acid. Particularly preferred agents for branching or cross-linking are hydroxycarboxylic acid units. Preferably the hydroxycarboxylic acid unit has two carboxyl groups and one hydroxyl group, two hydroxyl groups and one carboxyl group, three carboxyl groups and one hydroxyl group, or two hydroxyl groups and two carboxyl groups. In one preferred embodiment, the implants are prepared from poly(butylene succinate) comprising malic acid as a branching or cross-linking agent. The composition may be referred to as poly(1,4-butylene glycol-co-succinic acid), cross-linked with malic acid, poly(butylene succinate), cross-linked with malic acid, or succinic acid-1,4-butanediol-malic acid copolyester. It should be noted that the malic acid may dehydrate at high temperature, for example during melt extrusion, into maleic or fumaric acid units. It is intended that references herein to PBS copolymers comprising malic acid include implants where the malic acid in the PBS copolymer has undergone further reaction during processing, for example, to form maleic or fumaric acid or another compound. Thus, implants comprising poly(butylene succinate)-malic acid copolymer refer to implants prepared from copolymers comprising succinic acid, 1,4-butanediol and malic acid. In another preferred embodiment, malic acid may be used as a branching or cross-linking agent to prepare a copolymer of poly(butylene succinate) with adipate, which may be referred to as poly[(butylenesuccinate)-co-adipate] cross-linked with malic acid. The malic acid disclosed herein may be the L-enantiomer, D-enantiomer, a combination therefore, but in one preferred embodiment the poly (butylene succinate) is prepared using L-malic acid, such that poly(1,4-butylene glycol-co-succinic acid), cross-linked with L-malic acid is one particularly preferred composition.

Agents that may be used to chain extend poly(butylene succinate) or copolymer thereof also include epoxides, isocyanates, diisocyanates, oxazolines, diepoxy compounds, acid anhydrides, carbonates, silicate esters, and carbodiimides. Additional monomers may also be included that can be cross-linked, for example, maleic, fumaric, and itaconic acids can be incorporated and chains extended by the addition of peroxide. In one embodiment, copolymers with long-chain branching are preferred. It should be noted however that the use of isocyanates and diisocyanates is not preferred due to the toxicity associated with the use of these cross-linking chemistries. In one embodiment, the PBS and copolymer polymeric compositions exclude compositions prepared with isocyanates or diisocyanates. In another embodiment, the PBS and copolymer polymeric compositions exclude compositions prepared with urethane linkages. In a particularly preferred composition, the PBS and copolymer polymeric compositions used herein to prepare the implants are prepared only from monomers that have one or more of the following groups: hydroxy groups and carboxylic acid groups. In another embodiment, the PBS and copolymer thereof polymeric compositions exclude ether linkages.

In a preferred embodiment, the poly(butylene succinate) and copolymers thereof contain at least 70%, more preferably 80%, and even more preferably 90% by weight succinic acid and 1,4-butanediol units.

In another embodiment, the poly(butylene succinate) and copolymers thereof disclosed herein include polymers and copolymers in which known isotopes of hydrogen, carbon and/or oxygen are enriched. Hydrogen has three naturally occurring isotopes, which include $^1H$ (protium), $^2H$ (deuterium) and $^3H$ (tritium), the most common of which is the $^1H$ isotope. The isotopic content of the polymer or copolymer can be enriched for example, so that the polymer or copolymer contains a higher than natural ratio of a specific isotope or isotopes. The carbon and oxygen content of the polymer or copolymer can also be enriched to contain higher than natural ratios of isotopes of carbon and oxygen, including, but not limited to $^{13}C$, $^{14}C$, $^{17}O$ or $^{18}O$. Other isotopes of carbon, hydrogen and oxygen are known to one of ordinary skill in the art. A preferred hydrogen isotope enriched in polybutylene succinate) or copolymer thereof is deuterium, i.e., deuterated poly(butylene succinate) or copolymer thereof. The percent deuteration can be up to at least 1% and up to 5, 10, 15, 20, 25, 30, 35, 40, 45, 50, 55, 60 65, 70, 75, 80, or 85% or greater.

Preferred polymers and copolymers have a weight average molecular weight (Mw) of 10,000 to 400,000, more preferably 50,000 to 300,000 and even more preferably 100,000 to 200,000 based on gel permeation chromatography (GPC) relative to polystyrene standards. In a particularly preferred embodiment the polymers and copolymers have a weight average molecular weight of 50,000 to 300,000, and more preferably 75,000 to 300,000.

In a preferred embodiment, the tensile strength of an unoriented form of poly(butylene succinate) or copolymer thereof that is used to make the implants should be at least 1 MPa, preferably 10 MPa, more preferably 35 MPa, and even more preferably up to 70 MPa or higher. A particularly preferred tensile range for unoriented forms is 35-60 MPa. The Young's modulus of an unoriented form of poly(butylene succinate) or copolymer thereof that is used to make the implants should preferably be in the range of 30-700 MPa, and more preferably 300-500 MPa depending on its crystallinity. It is also preferable that the polymer or copolymer has a melting point of at least 80° C., preferably 90° C., and even more preferably greater than 100° C. In a preferred embodiment, the melting point of the poly(butylene succinate) or copolymer thereof that is used to make the implants is 115° C.±20° C., and more preferably between 105° C. and 120° C. A higher melting point (over 100° C.) is preferable to provide improved stability of the implants particularly during sterilization, shipping and storage.

In one preferred embodiment, the poly(butylene succinate) or copolymer thereof used to make the implants has one or more, or all of the following properties: density of 1.23-1.26 g/cm³, glass transition temperature of −31 C. to −35° C., melting point of 113° C. to 117° C., melt flow rate (MFR) at 190° C./2.16 kgf of 2 to 10 g/10 min, and tensile strength of 30 to 60 MPa.

In a particularly preferred embodiment, it is important that the poly(butylene succinate) or copolymer thereof, has a low moisture content during processing and storage. This is necessary to ensure that the implants can be produced with high tensile strength, prolonged strength retention, and good shelf life. In a preferred embodiment, the polymers and copolymers that are used to prepare the implants have a moisture content of less than 1,000 ppm (0.1 wt %), less than 500 ppm (0.05 wt %), less than 300 ppm (0.03 wt %), more preferably less than 100 ppm (0.01 wt %), and even more preferably less than 50 ppm (0.005 wt %).

The compositions used to prepare the implants must have a low endotoxin content. The endotoxin content must be low enough so that the implants produced from the poly(butylene succinate) or copolymer thereof have an endotoxin content of less than 20 endotoxin units per device as determined by the limulus amebocyte lysate (LAL) assay. In one embodiment, the compositions have an endotoxin content of <2.5 EU/g of PBS or copolymer thereof.

B. Additives and Other Polymers

Certain additives may be incorporated into poly(butylene succinate) and copolymers thereof prior to converting these compositions into resorbable implants. Preferably, these additives are incorporated during the compounding process to produce pellets that can be subsequently processed into implants. For example, additives may be compounded with poly(butylene succinate) or copolymer thereof, the compounded poly(butylene succinate) or copolymer thereof extruded into pellets, and the pellets 3D printed or extruded into fibers suitable for making implantable surgical meshes, for example by knitting, weaving or 3D printing. In another embodiment, the additives may be incorporated using a solution-based process. In a preferred embodiment of the invention, the additives are biocompatible, and even more preferably the additives are both biocompatible and resorbable.

In one embodiment of the invention, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the poly(butylene succinate) or copolymer thereof. Such agents may be used, for example, to improve the mechanical properties of fibers and meshes, as well as the implants, and to reduce cycle times. Preferred nucleating agents include, but are not limited to, salts of organic acids such as calcium citrate, polymers or oligomers of poly(butylene succinate) polymers and copolymers, high melting polymers such as polyglycolic and polylactic acids, alpha-cyclodextrin, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment of the invention, the additives are contrast agents, radiopaque markers and radioactive substances. These additives may also be incorporated into poly(butylene succinate) or copolymer thereof either before preparing the implants, such as fibers, meshes or 3D printed objects, or after they are prepared.

In yet another embodiment of the invention, the additives are other polymers, preferably other resorbable polymers. Examples of other resorbable polymers that can be incorporated into the compositions used to make the implants are: polymers and copolymers of glycolic acid, lactic acid, 1,4-dioxanone, trimethylene carbonate, ε-caprolactone, 3-hydroxybutyrate, 4-hydroxybutyrate, including polyglycolic acid, polylactic acid, polydioxanone, polycaprolactone, poly-4-hydroxybutyrate and copolymers thereof, poly-3-hydroxybutyrate, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers; polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks, and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone and copolymers thereof, including random copolymers and block copolymers thereof.

In one embodiment, the PBS or copolymer thereof polymeric composition is not blended with another polymer. In another embodiment, the PBS or copolymer thereof polymeric composition is not blended with polylactic acid (PLA).

C. Bioactive Agents

If desired, the implants of polybutylene succinate and copolymers thereof may incorporate bioactive agents. These bioactive agents may be added during the formulation process, during pelletization or blending, or may be added later to the implants.

Examples of bioactive agents that can be incorporated into the implants of poly(butylene succinate) or copolymer thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, antibiotics, antimicrobials, growth factors, fibronectin, laminin, vitronectin, integrins, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, anti-adhesion agents, hyaluronic acid and derivatives thereof, allograft material, xenograft material, ceramics, nucleic acid molecules, antisense molecules, aptamers, siRNA, nucleic acids, and combinations thereof. In a particularly preferred embodiment, the implants designed to allow tissue in-growth on one surface of the implant, and prevent tissue in-growth on another surface may be coated on the surfaces where tissue in-growth is not desired with a Sepra® hydrogel barrier. Such implants may be used, for example, in hernia repair to minimize tissue attachment to the visceral side of the implant following intraabdominal placement.

Antimicrobial agents that may be incorporated into the implants of poly(butylene succinate) and copolymers thereof, include, but are not limited to, antibacterial drugs, antiviral agents, antifungal agents, and antiparisitic drugs. Antimicrobial agents include substances that kill or inhibit the growth of microbes such as microbicidal and microbiostatic agents. Antimicrobial agents that may be incorporated into the implants of poly(butylene succinate) and copolymers thereof, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes. In a preferred embodiment, the antimicrobial agents incorporated into the implants are (i) rifampin and (ii) minocycline and its hydrochloride, sulfate, or phosphate salt. In a particularly preferred embodiment the implants of poly(butylene succinate) and copolymer thereof comprise rifampin and minocycline or its hydrochloride, sulfate, or phosphate salt.

III. Methods Of Synthesizing and Processing Implants of POLY(BUTYLENE SUCCINATE) and Copolymers Thereof A. Poly(butylene succinate) and Copolymers Thereof Poly(butylene succinate) and copolymers thereof may be synthesized by any suitable method. A suitable method must provide a biocompatible polymeric composition of PBS and copolymer thereof. In an embodiment, poly(butylene succinate) can be synthesized by (i) esterification of succinic acid and 1,4-butanediol or transesterification of dimethyl succinate and 1,4-butanediol to obtain oligomers, and (ii) polycondensation of the oligomers to form high weight average molecular weight poly(butylene succinate).

In one method, poly(butylene succinate) may be prepared by charging a suitable vessel with succinic acid (or dimethyl succinate) and 1,4-butanediol in a 1:1 ratio (or with a small excess of 1,4-butanediol). The reactants are heated to 130-190° C., more preferably 160-190° C., under an inert atmosphere, to melt the acid component and distill off water (or methanol). Once the distillation is completed, the pressure in the vessel is reduced using a high vacuum, and a suitable high weight average molecular weight poly(butylene succinate) is produced by polycondensation preferably at a temperature of 220-240° C. in the presence of a catalyst.

Suitable catalysts for the synthesis of poly(butylene succinate) include p-toluenesulfonic acid, tin (II) chloride, monobutyl tin oxide, tetrabutyl titanate, tetraisoproypl titanate, lanthanide triflates, and distannoxane. Catalysts may include metal elements of the Groups 1 to 14 of the periodic table. Preferred catalysts have metal elements that are scandium, yttrium, titanium, zirconium, vanadium, molybdenum, tungsten, zinc, iron and germanium. Titanium and zirconium catalysts are particularly preferred for preparing poly(butylene succinate) and copolymers thereof. Tetraalkyl titanates are preferred catalysts. Specifically, tetra-n-propyl titanate, tetraisopropyl titanate, tetra-n-butyl titanate, tetra-t-butyl titanate, tetraphenyl titanate, tetracyclohexyl titanate, tetrabenzyl titanate, and mixed titanates thereof are preferred. In addition, titanium (oxy)acetylacetonate, titanium tetraacetylacetonate, titanium (diisopropoxide) acetylacetonate, titanium bis(ammonium lactate) dihydroxide, titanium bis(ethylacetoacetate) diisopropoxide, titanium (triethanolaminate) isopropoxide, polyhydroxytitanium stearate, titanium lactate, titanium triethanolaminate, butyl titanate dimer, are also preferred catalysts. Of these, tetra-n-propyl titanate, tetraisopropyl titanate, and tetra-n-butyl titanate, titanium (oxy)acetylacetonate, titanium tetraacetylacetonate, titanium bis(ammonium lactate) dihydroxide, polyhydroxytitanium stearate, titanium lactate, and butyl titanate dimer are preferred, and tetra-n-butyl titanate, titanium (oxy)acetylacetonate, titanium tetraacetylacetonate, polyhydroxytitanium stearate, titanium lactate, and butyl titanate dimer are more preferred. Particularly, tetra-n-butyl titanate, polyhydroxytitanium stearate, titanium (oxy)acetylacetonate, and titanium tetraacetylacetonate are preferred. Zirconium catalysts that may be used to prepare the polymer or copolymer include zirconium tetraacetate, zirconium acetate hydroxide, zirconium tris(butoxy) stearate, zirconyl diacetate, zirconium oxalate, zirconyl oxalate, zirconium potassium oxalate, polyhydroxyzirconium stearate, zirconium ethoxide, zirconium tetra-n-propoxide, zirconium tetraisopropoxide, zirconium tetra-n-butoxide, zirconium tetra-t-butoxide, zirconium tributoxy acetylacetonate, and mixtures thereof. Of these, zirconyl diacetate, zirconium tris(butoxy) stearate, zirconium tetraacetate, zirconium acetate hydroxide, zirconium ammonium oxalate, zirconium potassium oxalate, polyhydroxyzirconium stearate, zirconium tetra-n-propoxide, zirconium tetraisopropoxide, zirconium tetra-n-butoxide, and zirconium tetra-t-butoxide are preferred, and zirconyl diacetate, zirconium tetraacetate, zirconium acetate hydroxide, zirconium tris(butoxy) stearate, zirconium ammonium oxalate, zirconium tetra-n-propoxide, and zirconium tetra-n-butoxide are more preferred. Particularly, zirconium tris(butoxy) stearate is preferred. Germanium catalysts that may be used include inorganic germanium compounds such as germanium oxide and germanium chloride and organic germanium compounds such as tetraalkoxygermanium. Germanium oxide, tetraethoxygermanium, tetrabutoxygermanium, and the like are preferred. Other metal-containing catalysts that can be used include scandium compounds such as scandium carbonate, scandium acetate, scandium chloride, and scandium acetylacetonate, yttrium compounds such as yttrium carbonate, yttrium chloride, yttrium acetate, and yttrium acetylacetonate, vanadium compounds such as vanadium chloride, vanadium oxide trichloride, vanadium acetylacetonate, and vanadium acetylacetonate oxide, molybdenum compounds such as molybdenum chloride and molybdenum acetate, tungsten compounds such as tungsten chloride, tungsten acetate, tungstenic acid, lanthanoid compounds such as cerium chloride, samarium chloride, and ytterbium chloride.

When a metal compound is used as a catalyst, the amount of catalyst used to prepare poly(butylene succinate) or copolymer thereof is preferably 0.1 ppm or more, preferably 0.5 ppm or more, more preferably 1 ppm or more, and less than 30,000 ppm, preferably less than 1,000 ppm, more preferably less than 250 ppm, and more preferably less than 130 ppm.

After completion of the polycondensation, the polymer can be purified by dissolution in a solvent, filtering, and precipitation. For example, the polymer can be dissolved in chloroform, filtered, and precipitated with an alcohol such as methanol or ethanol. If desired, the polymer may be further purified by washing, for example with diethyl ether. Preferably the amount of metal in the poly(butylene succinate) or copolymer thereof is less than 100 ppm, and more preferably less than 50 ppm. A preferred metal content in the poly(butylene succinate) or copolymer thereof is 0.1-100 ppm, and more preferably 1-50 ppm.

In an embodiment, the polymeric compositions of PBS and copolymer thereof used to prepare the implants comprise 1-500 ppm of one or more of the following: silicon, titanium and zinc. Preferably, the polymeric compositions comprise less than 50 ppm of silicon, titanium and zinc. In another embodiment, the polymeric compositions used to make the implants do not comprise metals other than silicon, titanium and zinc in detectable quantities by PIXE analysis. In a particularly preferred embodiment, the polymeric compositions used to make the implants exclude tin.

Copolymers of poly(butylene succinate) may be formed by copolymerization with different comonomer units, preferably dicarboxylic acids and diols, including for example, adipic acid, terephthalic acid, fumaric acid, ethylene glycol and 1,3-propanediol. Other suitable diol and dicarboxylic acid comonomer units include 1,2-propanediol, 1,2-butanediol, 1,3-butanediol, 2,3-butanediol, 1,5-pentane diol, 1,2-pentanediol, 2,4-pentanediol, 1,6-hexanediol, 1,2-hexanediol, suberic acid, sebacic acid, azelaic acid, decanedicarboxylic acid, dodecanedicarboxylic acid, and octadecanedicarboxylic acid. In a preferred embodiment, the content of comonomer units is less than 30%, more preferably less than 20% and even more preferably less than 15%. In another preferred embodiment, the comonomer content of the copolymer is less than 15%, and the melting point of the comonomer is more than 100° C. Preferably, the melting point of the PBS copolymer is between 105° C. and 120° C.

In yet another embodiment, the polymers and copolymers of succinic acid and 1,4-butanediol may contain chain branches, most preferably chain branches formed with aliphatic oxycarboxylic acids. Preferred chain branching agents are trifunctional and tetrafunctional aliphatic oxycarboxylic acids. Preferred trifunctional oxycarboxylic acid chain branching agents may have (i) two carboxyl groups and one hydroxyl group in the same molecule (such as malic acid), or (ii) one carboxyl group and two hydroxyl groups in the same molecule. Preferred tetrafunctional oxycarboxylic acid chain branching agents may have (i) three carboxyl groups and one hydroxyl group in the same molecule (such as citric acid), (ii) two carboxyl groups and two hydroxyl groups in the same molecule (such as tartaric acid), or (iii) three hydroxyl groups and one carboxyl group in the same molecule. Other chain branching agents that may be incorporate include hydroxyglutaric acid, hydroxymethylglutaric acid, hydroxyisophthalic acid, and hydroxyterephthalic acid. Malic acid, tartaric acid and citric acid are particularly preferred chain branching agents. Chain branching agents, cross-linking agents, coupling agents and chain extending agents are preferably incorporated into the poly(butylene succinate) and copolymer thereof in amounts of 0.01 to 5.0 mol %, more preferably 0.01 to 2.5 mol %, and most preferably 0.1 to 0.5 mol %. In one embodiment, the chain branching agent is malic acid. In a preferred embodiment, malic acid is incorporated in the poly(butylene succinate) polymer or copolymer in an amount of 0.01-5.0 mol %, more preferably 0.1-0.5 mol %, or in an amount of 0.01-1 part by weight, more preferably 0.1-0.5 parts by weight. When malic acid is used as a trifunctional oxycarboxylic acid serving as the copolymerizable component, examples of the copolyester include succinic acid-1,4-butanediol-malic acid copolyester, succinic acid-adipic acid-1,4-butanediol-malic acid copolyester, succinic acid-1,4-butanediol-malic acid-tartaric acid copolyester, succinic acid-adipic acid-1,4-butanediol-malic acid-tartaric acid copolyester, succinic acid-1,4-butanediol-malic acid-citric acid copolyester, and succinic acid-adipic acid-1,4-butanediol-malic acid-citric acid copolyester. Malic acid may be present as the L-enantiomer, D-enantiomer, or both, but L-malic acid is preferred. During exposure to heat, or further processing, the malic acid monomers in the copolymer may dehydrate to produce fumaric and maleic acids monomers in the copolymer. Thus, the implant disclosed herein may also comprise fumaric and maleic acid units, or combinations thereof.

B. Spinning of Poly(butylene succinate) and Copolymers Thereof

Poly(butylene succinate) and copolymers thereof may be processed and oriented to provide implants with high tensile strength and prolonged strength retention. The polymers may be processed in the melt or in solution. In one preferred embodiment, poly(butylene succinate) and copolymers thereof are melt processed.

In melt processing of poly(butylene succinate) and copolymers thereof it is important to prevent hydrolysis of the polymers by residual moisture. Therefore, it is important that the polymers are dried prior to melt processing. In a preferred embodiment, the poly(butylene succinate) and copolymers are dried prior to melt processing so that they have a moisture content of less than 0.1 wt. %, preferably less than 0.05 wt. %, more preferably less than 0.01 wt. %, and even more preferably less than 0.005 wt. %. The polymers may be dried with hot air and under vacuum prior to melt processing. In a preferred embodiment, the polymers are dried under vacuum at 30-90° C., more preferably 60-90° C.

In order to obtain implants with high tensile strength and prolonged strength retention, it is important to prevent loss of weight average molecular weight during melt processing of poly(butylene succinate) and copolymers thereof. At temperatures in excess of 200° C., the shear viscosity of poly(butylene succinate) can decrease significantly. The magnitude of the loss increases as the temperature rises above 200° C. and as the exposure time increases. In order to make implants with the highest tensile strength and prolonged strength retention, it is therefore important to minimize the time the polymers are exposed to high processing temperatures as well as the presence of moisture in the polymers. In an embodiment, the implants are melt extruded with a temperature profile of 60-230° C., more preferably 80-180° C., and even more preferably 80-170° C.

Examples 1 and 2 described herein compare two different methods of melt extruding poly(butylene succinate) and copolymers thereof. It has been discovered that the method disclosed in Example 2 yields fibers with substantially higher tensile strengths than those obtained by the method described in Example 1. Thus, the method disclosed in Example 2 is preferred for making implants comprising fibers when it is desirable for the fibers to have high tensile strength and prolonged strength retention. Using the method disclosed in Example 2, fibers were obtained with tensile strengths of 779-883 MPa compared to tensile strengths of 434-518 MPa produced by the method disclosed in Example 1. In contrast to the method of Example 1, the use of multi-stage incremental orientation of the fiber and use of conductive chambers, instead of standard convention chambers used in Example 1, resulted in fiber with surprisingly higher tensile strengths. In a preferred embodiment, monofilament or multifilament fiber comprising poly(butylene succinate) and copolymers thereof is produced by a method comprising the steps of: (a) spinning multifilament or monofilament fiber comprising the polymer composition, (b) one or more stages of drawing the multifilament or monofilament fiber with an orientation ratio of at least 3.5 at a temperature of 50-70° C., (c) one or more stages of drawing the multifilament or monofilament fiber with an orientation ratio of at least 2.0 at a temperature of 65-75° C., and (d) drawing the multifilament or monofilament fiber with an orientation ratio greater than 1.0 at a temperature of 70-75° C. Preferably, the sum of the orientation ratios is over 6.0, 6.5, 7.0, 7.5 or 8.0. In an even more preferred embodiment, the fibers are drawn in a conductive liquid chamber. Prior to drawing the fibers, melt extruded polymer is preferably quenched in a conductive liquid bath. The temperature of the bath is preferably from 50° C. to 70° C. Further cooling of the fiber after it is quenched may be desired, and can be achieved by passing the fiber between two godets. In an embodiment, the temperature range for extrusion of PBS or copolymer thereof to form high strength fibers is from 60-230° C., or 75-220° C., but is more preferably from 75-200° C., 80-180° C., 80-175° C., or 80-170° C. Example 3 discloses specific examples of a method using multi-stage incremental orientation and the use of conductive chambers to prepare multifilament fibers of PBS and copolymers thereof. Examples of multifilament fibers with tenacities of 8.3-12.5 g/d are shown.

If desired, the oriented fibers may be annealed. In one embodiment, the oriented fibers may be annealed using temperatures of 80° C. to 120° C., and more preferably 105° C.±10° C.

In an embodiment, the oriented monofilament fibers have diameters ranging from 0.01 to 1.00 mm. In a particularly preferred embodiment, the diameters of the monofilament fibers range from 0.07 to 0.7 mm. In another embodiment, the monofilament fibers may optionally meet the USP standards for absorbable monofilament sutures.

In an embodiment, the monofilament fibers of PBS and copolymers thereof have a tensile strength of 400 MPa to 2,000 MPa, and more preferably a tensile strength greater than 500 MPa, 600 MPa, 700 MPa or 800 MPa, but less than 1,200 MPa. In another embodiment, the monofilament fibers of PBS and copolymer thereof have a Young's Modulus of at least 600 MPa, and less than 3 GPa, but more preferably greater than 800 MPa, 1 GPa, 1.5 GPa, and 2 GPa. In a further embodiment, the monofilament fibers of PBS and copolymer thereof have an elongation to break of 10-150%, and more preferably 10-50%.

In yet another embodiment, the multifilament fibers of PBS and copolymers thereof have a tenacity greater than 4 grams per denier, but less than 14 grams per denier. Preferably, the multifilament fibers have an elongation to break of between 15% and 50%.

The yarns and monofilament fibers of poly(butylene succinate) and copolymers thereof may be used to prepare knitted and woven meshes, non-woven meshes, suture tapes, mesh sutures, webs, and patches. These mesh, web, and patch products are particularly useful for soft tissue repair, hernia repair, breast lifts, breast reconstructions, face and neck lifts, pelvic floor reconstruction, treatment of stress urinary incontinence, organ salvage, lift and suspension procedures, and for making enclosures, pouches, holders, covers, clamshells, and casings to hold implantable medical devices.

In view of their mechanical properties, the yarns and monofilament fibers disclosed herein may also be used to prepare medical devices including sutures, braided sutures, hybrid sutures of monofilament and multifilament fibers, barbed sutures, suture tapes, mesh sutures, braids, ligatures, tapes, knitted or woven meshes, knitted tubes, multifilament meshes, patches, wound healing devices, bandages, wound dressings, burn dressings, ulcer dressings, skin substitutes, hemostats, tracheal reconstruction devices, organ salvage devices, dural substitutes, dural patches, nerve regeneration or repair devices, hernia repair devices, hernia meshes, hernia plugs, device for temporary wound or tissue support, tissue engineering scaffolds, guided tissue repair/regeneration devices, anti-adhesion membranes, adhesion barriers, tissue separation membranes, retention membranes, slings, devices for pelvic floor reconstruction, urethral suspension devices, devices for treatment of urinary incontinence, devices for treatment of vesicoureteral reflux, bladder repair devices, sphincter muscle repair devices, suture anchors, soft suture anchors, bone anchors, ligament repair devices, ligament augmentation devices, ligament grafts, anterior cruciate ligament repair devices, tendon repair devices, tendon grafts, tendon augmentation devices, rotator cuff repair devices, meniscus repair devices, meniscus regeneration devices, articular cartilage repair devices, osteochondral repair devices, spinal fusion devices, stents, including coronary, cardiovascular, peripheral, ureteric, urethral, urology, gastroenterology, nasal, ocular, or neurology stents, stent grafts, cardiovascular patches, vascular closure devices, intracardiac septal defect repair devices, including but not limited to atrial septal defect repair devices and PFO (patent foramen ovale) closure devices, left atrial appendage (LAA) closure devices, pericardial patches, vein valves, heart valves, vascular grafts, myocardial regeneration devices, periodontal meshes, guided tissue regeneration membranes for periodontal tissue, embolization devices, anastomosis devices, cell seeded devices, controlled release devices, drug delivery devices, plastic surgery devices, breast lift devices, mastopexy devices, breast reconstruction devices, breast augmentation devices (including devices for use with breast implants), breast reduction devices (including devices for removal, reshaping and reorienting breast tissue), devices for breast reconstruction following mastectomy with or without breast implants, facial reconstructive devices, forehead lift devices, brow lift devices, eyelid lift devices, face lift devices, rhytidectomy devices, thread lift devices (to lift and support sagging areas of the face, brow and neck), rhinoplasty devices, device for malar augmentations, otoplasty devices, neck lift devices, mentoplasty devices, buttock lift devices, cosmetic repair devices, devices for facial scar revision, and enclosures, pouches, holders, covers, clamshells, casings to hold implantable medical devices.

C. 3D Printing of Implants

In another preferred embodiment, the implants may be prepared by 3D printing. Methods that can be used to 3D print poly(butylene succinate) and copolymers thereof include fused filament fabrication (FFF), fused pellet deposition, melt extrusion deposition (MED), selective laser melting, and solution printing.

A particularly preferred method of 3D printing poly (butylene succinate) and copolymers thereof is to feed a filament of the polymer or copolymer to a FFF printer. In FFF of poly(butylene succinate) and copolymers it is important to prevent hydrolysis of the polymers by residual moisture. Therefore, it is important that the filament used in FFF has a low moisture content, preferably less than 0.1 wt. %, preferably less than 0.05 wt. %, more preferably less than 0.01 wt. %, and even more preferably less than 0.005 wt. %. The filament may be dried with hot air and under vacuum prior to printing. In a preferred embodiment, the polymers are dried under vacuum at 30-90° C., more preferably 60-90° C.

In order to obtain 3D printed implants with high tensile strength and prolonged strength retention, it is important to prevent loss of weight average molecular weight during melt processing of poly(butylene succinate) and copolymers thereof. The magnitude of the molecular weight loss increases as the temperature rises above 200° C. and as the exposure time increases. In order to make implants with the highest tensile strength and prolonged strength retention, it is therefore important to minimize the time the polymers are exposed to high processing temperatures during 3D printing as well as the presence of moisture in the polymer or copolymer. The temperature of the hot end, including the printer nozzle, may be set to temperatures ranging from 120° C. to 300° C., more preferably 130° C. to 230° C., and even more preferably 150° C. to 200° C.

Methods of 3D Printing of PBS and copolymers thereof are shown in Examples 9 and 10. The 3D Printing of a PBS-malic acid copolymer by MED using different thermal conditions is shown in Example 18, and the properties of the implants obtained shown in Table 17. Surprisingly, the weight average molecular weight of the PBS polymer was found to increase as the processing temperature was raised from 180° C. to 220° C. (At 230° C., the weight average molecular weight decreased from the peak at 220° C.) An increase in molecular weight can be particularly advantageous in some implant applications. For example, increasing the weight average molecular weight can result in prolonged strength retention of the implant. In an embodiment, implants comprising PBS and copolymers thereof, are produced with weight average molecular weights that exceed the weight average molecular weights of the composition used to prepare the implants. The implants may be formed by 3D Printing, including fused filament fabrication, fused pellet deposition, melt extrusion deposition, and selective laser melting, but also using other thermal processing techniques, such as melt processing, melt extrusion, melt-blowing, melt spinning, injection molding, compression molding, lamination, foaming, film extrusion, thermoforming, pultrusion, molding, tube extrusion, spun-bonding, nonwoven fabrication. In an embodiment, implants comprising PBS and copolymers thereof, may be formed by melt processing with weight average molecular weights that are between 1-50%, more preferably 5-30%, higher than the weight average molecular weights of the PBS and copolymers resins used to prepare the implants.

D. Other Methods of Manufacturing Implants

Implants comprising poly(butylene succinate) and copolymers thereof may also be prepared by casting, solvent casting, solution spinning, solution bonding of fibers, melt processing, extrusion, melt extrusion, melt spinning, fiber spinning, orientation, relaxation, annealing, injection molding, compression molding, lamination, particle formation, microparticle, macroparticle and nanoparticle formation, foaming, dry spinning, knitting, weaving, crocheting, melt-blowing, film formation, film blowing, film casting, membrane forming, electrospinning, thermoforming, pultrusion, centrifugal spinning, molding, tube extrusion, spunbonding, nonwoven fabrication, entangling of staple fibers, fiber knitting, weaving and crocheting, mesh fabrication, coating, dip coating, laser cutting, barbing, barbing of fibers, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, and printing using a binding solution and granules of powder.

E. Antimicrobial Coatings

In an embodiment, the implants comprising poly(butylene succinate) and copolymers thereof, may be coated with solutions of antimicrobial agents dissolved in poor solvents for poly(butylene succinate) and copolymers thereof. These poor solvents do not cause significant loss of orientation, if any, of the poly(butylene succinate) or copolymer thereof. However, these poor solvents allow the antimicrobial agents to slightly soften and penetrate the surfaces of the implants. This has two main advantages. First, it allows the implants to be coated with higher concentrations of antimicrobial agents, and second it allows the antimicrobial agents to diffuse into the implants. Diffusion of the antimicrobial agents into the implants results in a more prolonged release profile, and an increased ability of the implant to prevent colonization of the implants, and reduce or prevent the occurrence of infection following implantation in a patient. A suitable poor solvent that can dissolve antimicrobial agents, but not cause loss of orientation of the implants, is an aqueous or alcoholic solution of tetrahydrofuran (THF). Alcohols that may be combined with this solvent includes methanol and ethanol. The concentration of the antimicrobial agent(s) in the poor solvent can range from about 0.1 mg/mL to about 100 mg/mL, preferably from about 1 mg/mL to about 30 mg/mL. The amount (density of coverage) of each antimicrobial coated on the implant can range from about 1 $\mu g/cm^2$ to about 1000 $\mu g/cm^2$, or preferably, from about 50 $\mu g/cm^2$ to about 200 $\mu g/cm^2$. In various embodiments, the amount ranges from about 10 $\mu g/cm^2$ to about 175 $\mu g/cm^2$, or from about 10 $\mu g/cm^2$ to about 150 $\mu g/cm^2$, or from about 10 $\mu g/cm^2$ to about 100 $\mu g/cm^2$, or from about 10 $\mu g/cm^2$ to about 75 $mg/cm^2$, or from about 20 $\mu g/cm^2$ to about 200 $\mu g/cm^2$ or from about 50 $\mu g/cm^2$ to about 200 $\mu g/cm^2$, or from about 75 $\mu g/cm^2$ to about 200 $\mu g/cm^2$ or from about 100 $\mu g/cm^2$ to about 200 $\mu g/cm^2$, or from about 150 $\mu g/cm^2$ to about 200 $\mu g/cm^2$.

In a preferred embodiment of the invention, the implants of poly(butylene succinate) and copolymers thereof, are coated with rifampin and minocycline (including its hydrochloride, sulfate, or phosphate salt) dissolved in poor solvents for poly(butylene succinate) and copolymers thereof. The antimicrobial agents may be applied to the oriented implants individually using the same or different poor solvents, or from a single solution containing both antimicrobial agents in a poor solvent. In one embodiment, rifampin may be applied to the implants of poly(butylene succinate) and copolymers thereof from solutions of the following poor solvents (i) THF, (ii) DMSO, (iii) DMF and (iv) DMA each mixed with one or more of the following: water, methanol and/or ethanol. In another embodiment, minocycline may be applied to the oriented implants of poly(butylene succinate) and copolymers thereof from solutions in the following poor solvents: THF/water, THF/methanol, and THF/ethanol. In a preferred embodiment, rifampin and minocycline (including its hydrochloride, sulfate, or phosphate salt forms) are dissolved in a solution of THF/water, THF/ethanol or THF/ethanol, and applied to the implants.

F. Sterilization of the Implants

Implants made from the high tenacity yarns and monofilament fibers of poly(butylene succinate) and copolymers thereof, or from other implants of poly(butylene succinate) and copolymers thereof, may be sterilized using ethylene oxide gas, and even more preferably using an ethylene oxide cold cycle. In another preferred embodiment, the implants may be sterilized with electron-beam irradiation or gamma-irradiation. In another embodiment, the implants may be sterilized using alcohol. The sterility of the devices may be maintained by packaging of the devices in packages designed to protect the devices from contamination and maintain sterility.

IV. Implants Of POLY(BUTYLENE SUCCINATE) and Copolymers Thereof

The compositions of poly(butylene succinate) and copolymers thereof described herein are suitable for preparing implants for soft and hard tissue repair, regeneration, and replacement.

Implants of oriented forms of poly(butylene succinate) and copolymers thereof are particularly suitable for use in applications requiring prolonged strength retention. The multifilament yarns and monofilament fibers disclosed herein have prolonged strength in vivo making them suitable for soft tissue repairs where high strength is required and where strength needs to be maintained for a prolonged period. Other examples of applications for the high strength yarn and monofilament fibers include soft and hard tissue repair, replacement, remodeling, and regeneration include wound closure, breast reconstruction and breast lift, including mastopexy procedures, lift procedures performed on the face such as face-lifts, neck lifts, and brow lifts, ligament and other tendon repair procedures, abdominal closure, hernia repairs, anastomosis, slings for lifting tissues, slings for treatment of stress urinary incontinence, and pelvic floor reconstruction.

A. Sutures and Braids

Figure 5:
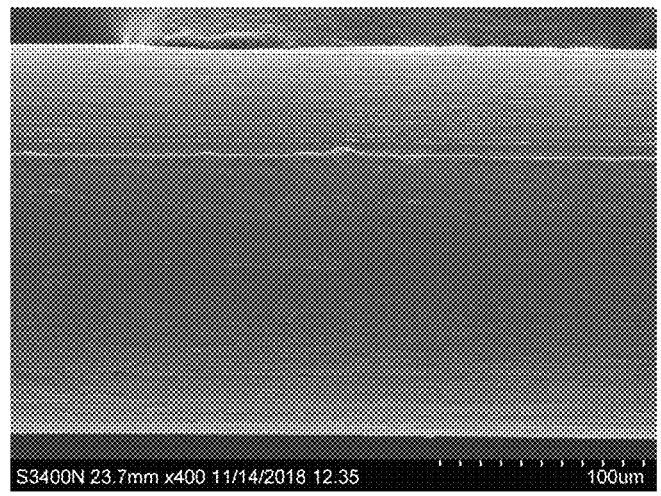
FIG. 5 is a SEM image of an oriented PBS monofilament suture fiber after implantation at a rabbit subcutaneous site for 4 weeks. The image shows a smooth surface with no surface pitting or localized erosion of the surface at a 400× magnification.

It has been discovered that oriented fibers of PBS and copolymers thereof have prolonged strength retention when implanted in vivo, as shown in Examples 16 and 15. FIG. 5 is a SEM of an oriented fiber that has been explanted after 4 weeks. Surprisingly, the surface of the fiber shows little if any noticeable surface pitting or localized surface erosion at a 400× magnification. The result is surprising in view of the known surface erosion and pitting of fibers derived from other resorbable fibers. The finding makes it possible to use the fibers in applications where prolonged strength retention is required. The lack of surface erosion is particularly important for strength retention of small diameter fibers where pitting of the surface of the fiber can rapidly decrease strength retention. The fibers are also useful in applications where high initial tensile strength is required. Example 16 clearly shows that an oriented fiber, when implanted in vivo, does not lose a significant amount of tensile strength in the first 4 weeks. The study described in Example 15 further demonstrates that a mesh made from oriented fiber of PBS or copolymer thereof retains 74.1% of its strength after 12 weeks indicating prolonged strength retention of the fibers. Analysis of the weight average molecular weights of the implanted fibers after 4 and 12 weeks in these studies shows that the fiber is degrading. The weight average molecular weight of the suture fiber in Example 16 decreases 7.3% to 92.7% of the initial value at 4 weeks, and the weight average molecular weight of the fiber in the mesh decreases 25.9% to 74.1% of the initial value at 12 weeks. It is also clear that there is good correlation between the weight average molecular weight loss of oriented fibers of PBS and copolymers thereof in vitro, shown in Example 12, with the in vivo data shown in Examples 15 and 16. This good correlation is further evidence that the oriented fibers resist surface pitting or surface erosion.

In a preferred embodiment, the weight average molecular weight of the fibers of PBS or copolymer thereof decrease 3 to 15% over a 4-week period in vivo, 5% to 15% over an 8-week time period, or 10-35%, more preferably 10-30%, over a 12-week time period, under physiological conditions, in vivo. The percent mass loss of the fibers is preferably between 0% and 5% over a 4-week period, under physiological conditions, in vivo.

In an embodiment, the monofilament fibers used to prepare sutures, suture meshes, braids, and tapes have a tensile strength between 400 MPa and 2,000 MPa, and more preferably greater than 500 MPa, 600 MPa, 700 MPa or 800 MPa, and less than 1,200 MPa. Preferably the monofilament fibers used to prepare the sutures, suture meshes and tapes have a Young's Modulus between 600 MPa and 3 GPa, but preferably at least 800 MPa, 1 GPa or 2 GPa. It has been found that the high Young's Modulus of the fiber prevents the suture from forming pig tails, or curling, during suturing. In another preferred embodiment, the monofilament fibers used to prepare sutures, suture meshes, braids, and tapes have a melting temperature over 100° C., and preferably 105° C. to 120° C.

The monofilament fibers of poly(butylene succinate) and copolymers thereof may also be used to prepare high strength monofilament sutures, hybrid sutures of monofilament and multifilament fibers that have good pliability, high knot strength, and can be securely knotted with low profile knot bundles (i.e. secured with a few throws). In one embodiment, the monofilament fibers may be processed into resorbable high strength sutures and suture anchors that can be used, for example, in rotator cuff repair procedures. These sutures and anchors are particularly useful for shoulder, elbow, wrist, hand hip, knee, ankle, and foot repairs, including tendon and ligament repairs, as well as in soft tissue approximation, ligation of soft tissue, abdominal closure, and plastic surgery procedures such as lift and suspension procedures, including face and breast lift procedures and breast reconstruction. The monofilament sutures and suture anchors (including soft suture anchors) may incorporate one or more needles, be transparent or dyed, and if desired, braided as part of a suture or suture anchor, or braided into flat tapes.

The monofilament fibers of poly(butylene succinate) and copolymers thereof may also be used to prepare barbed sutures.

It has been discovered that multifilament fiber of poly (butylene succinate) and copolymers thereof may be used to prepare high strength multifilament sutures, hybrid sutures of monofilament and multifilament fibers that have excellent pliability, prolonged strength retention, high knot strength, good drape, and can be securely knotted forming soft knot bundles with a low profile. Example 3 discloses one method that can be used to produce high strength multifilament of PBS or copolymers thereof suitable for use in these applications.

Multifilament yarns of PBS and copolymers thereof may be processed into resorbable high strength sutures and suture anchors that can be used in rotator cuff repair procedures. Currently, these procedures are repaired with permanent sutures because existing resorbable sutures degrade too quickly. In contrast to existing resorbable sutures, sutures prepared with the high tenacity yarn of the present invention not only provide high initial strength to stabilize a repair under a significant load, but also lose strength slowly allowing the repair of the soft tissues. The high strength sutures may also be used in bone anchors, suture anchors, and soft suture anchors. These sutures and anchors are particularly useful for shoulder, elbow, wrist, hand hip, knee, ankle, and foot repairs, including tendon and ligament repairs, as well as in lift and suspension procedures. The bone anchors, suture anchors and soft suture anchors may incorporate one or more needles, yarns of different colors, and if desired, flat braided sections. The ability to use resorbable high tenacity sutures, suture anchors, bone anchors, and soft suture anchors for procedures such as rotator cuff repair eliminates longer-term complications that can arise from foreign bodies, such as permanent sutures. These sutures may be used, for example, in soft tissue approximation, anastomosis, suspension and lift procedures, and for other applications in plastic surgery.

In one preferred embodiment, the yarns of poly(butylene succinate) and copolymers thereof may be used to prepare high strength braided sutures wherein the breaking load of the sutures is between 40 N and 270 N. In a particularly preferred embodiment, the high tensile strength braided sutures comprising poly(butylene succinate) and copolymers thereof have a strength retention in vivo under physiological conditions of at least 40% after implantation for 4-6 months.

Suture braids may be produced from the yarns with US Pharmacopeia (USP) suture sizes of 12-0, 11-0, 10-0, 9-0, 8-0, 7-0, 6-0, 5-0, 4-0, 3-0, 2-0, 0, 1, 2, 3, 4, and 5, and meet the USP knot-pull tensile strengths or breaking loads for these sizes. In another embodiment, the suture braids may be oversized in diameter in order to meet USP knot-pull tensile strengths or breaking loads. For example, the diameter of the suture braids maybe oversized by up to 0.3 mm, preferably 0.2 mm, more preferably 0.1, and even more preferably 0.05 mm. The sutures may be needled and/or contain loops at either end.

In another embodiment, the yarns of poly(butylene succinate) and copolymers thereof and monofilaments of poly (butylene succinate) and copolymers thereof, may be used to prepare flat suture tapes, including flat braided suture tapes. These suture tapes are useful in approximation and/or ligation of soft tissue, and are particularly useful in procedures requiring broad compression and increased cut-through resistance. For example, the suture tapes can be used in shoulder and rotator cuff repair procedures such as acromioclavicular repairs, and restoration of labral height in instability repairs, as well as in ACL and PCL repair procedures. The suture tapes may have flat ends, tapered ends, needles at one or both ends of the suture tape, and comprise yarns with one or more different dyes.

Suture tapes disclosed herein may also be used as slings for tissue support, including slings for treatment of stress urinary incontinence.

In another embodiment, coatings may be applied to increase the lubricity of the braided sutures, and other fiber-based implants. These coatings include wax, natural and synthetic polymers such as polyvinyl alcohol, and spin finishes including polyethylene glycol sorbitan monolaurate, and polymers or oligomers of ethylene oxide, propylene oxide, PEG400, PEG40 Stearate, Dacospin and Filapan. These coatings are preferably applied so the braided suture has a coating weight of less than 6 wt. %, more preferably less than 3 wt. %, and even more preferably less than 2 wt. %. It is preferred that the coatings readily leave the surface of the braided suture or fiber-based device in vivo, for example, by degradation or dissolution (for example if the coating is water-soluble.)

In another embodiment, a coating may be applied to the surface of the suture in order to slow degradation and increase strength retention in vivo. For example, the suture may be coated with another polymer, preferably a slowly degrading polymer or composition, or coated with wax. For example, the suture may be coated with polycaprolactone to slow degradation, and prolong strength retention further.

Braids (including suture tapes and suture braids) made from high tenacity yarns of poly(butylene succinate) and copolymers thereof are preferably prepared by coating the yarn with spin finish, twisting or plying the yarn, and winding onto bobbins. Preferred spin finishes are polyethylene glycol sorbitan monolaurate and polyethylene glycol. The bobbins are then placed on a braider. The number of picks per inch may be increased to improve the fineness of the braid, as desired. The number of picks per inch can range from 5 to 100, and preferably 30 to 60. In some embodiments, cores of monofilament, yarn, or multiple plied yarn strands may be incorporated into the center of the braid. Alternatively, the braids may be prepared without cores. For example, to produce hollow braids.

In an embodiment, the yarns and monofilament fibers of poly(butylene succinate) and copolymers thereof may be used to prepare mesh sutures that can spread the load placed on re-apposed tissues, and thereby reduce suture pull-through (cheese wiring effect) and wound dehiscence. The mesh sutures may be threaded through tissue, the mesh anchored in tissue under tension to re-appose soft tissue, and the needle removed. The use of mesh instead of suture fiber to re-appose tissues increases the strength of the repair. The porosity of the mesh is designed to allow the in-growth of tissue into the mesh.

The mesh sutures comprise a suture needle and a mesh component. The mesh component comprises fibers of poly (butylene succinate) and copolymers described herein, and preferably monofilament fibers of poly(butylene succinate) and copolymers thereof. The mesh component is an interlaced structure of fibers, preferably monofilament fibers of poly(butylene succinate) and copolymers thereof. Preferably the mesh structure is formed by knitting, braiding and weaving of fibers comprising poly(butylene succinate) and copolymers thereof, and most preferably monofilament fibers. The cross-section of the mesh component may be an ellipse, half-ellipse, circle, half-circle, gibbous, rectangle, square, crescent, pentagon, hexagon, concave ribbon, convex ribbon, H-beam, I-beam or dumbbell-shaped. Alternatively, the mesh component may assume these shapes as it is passed through tissue. Preferably, the mesh component flattens as it is passed through tissue. The mesh component may also have a cross-sectional profile that varies over the length of the mesh. For example, part of the cross-section of the mesh may be tubular, and another part non-tubular. However, in a preferred embodiment, the mesh has the same cross-section as the suture needle, and more preferably a cross-section with dimensions that are no more than ±25% of the cross-section of the suture needle. The mesh preferably has pores with average diameters ranging from 5 μm to 5 mm, and more preferably 50 μm to 1 mm. The width of the mesh is preferably from 1 mm to 20 mm, more preferably 1 mm to 10 mm, and even more preferably 1 mm to 7.8 mm. The width may vary along the length of the mesh. In an embodiment, the mesh may have an elasticity similar to the tissue at the site of implantation. For example, in the case of the repair of abdominal tissue, the mesh suture preferably has the same elasticity, or a similar elasticity to abdominal tissue. In another embodiment, the elasticity of the mesh is designed to permit even greater tension to be applied to the re-apposed tissues in order to keep the re-apposed tissue approximated to one another. Preferably, the mesh suture will stretch less than 30%, and more preferably less than 20%. It is also desirable that the mesh has sufficient flexibility to allow it to be passed through tissues with tight curvatures. In a preferred embodiment, the mesh suture has a stiffness less than 5 Taber Units (TU), more preferably less than 1 TU, and even more preferably less than 0.8 TU. In yet another embodiment, the mesh suture has an in vivo strength retention under physiological conditions of at least 75% at 4 weeks, more preferably at least 80% at 4 weeks, and even more preferably at least 65% at 12 weeks.

The sutures, braids, suture tapes, mesh sutures, meshes, patches and circular knits made from the high tenacity yarns and monofilament fibers of poly(butylene succinate) and copolymers thereof may be used in ligament and tendon repairs, hernia repairs, pelvic floor reconstruction, pelvic organ prolapse repair, Bankart lesion repair, SLAP lesion repair, acromion-clavicular repair, capsular shift/capsulolabral reconstruction, deltoid repair, Labral repair of the shoulder, Capsular/Labral Repairs of the Hip, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, VMO advancement, knee joint capsule closure, hand and wrist collateral ligament repair, scapholunate ligament reconstruction, tendon transfers in phalanx, volar plate reconstruction, acetabular labral repair, anterior ligament repair, spinal repair, fracture fixation, cardiovascular surgery, general surgery, gastric surgery, bowel surgery, abdominoplasty, plastic, cosmetic and reconstructive surgery including lift procedures, forehead lifting, brow lifting, eyelid lifting, facelift, neck lift, breast lift, lateral canthopexy, elevation of the nipple, breast reconstruction, breast reduction, breast augmentation, mastopexy, cystocele and rectocele repair, low anterior resection, urethral suspension, obstetrics and gynecological surgery, Nissen Fundoplication, myomectomy, hysterectomy, sacrolpopexy, cesarean delivery, general soft tissue approximation and ligation, wound closure including closure of deep wounds and the reduction of wide scars and wound hernias, hemostasis, anastomosis, abdominal closure, reinforcement of suture repairs, laparoscopic procedures, partial nephrectomy, vascular grafting, and implantation of cardiac rhythm management (CRM) devices, including pacemakers, defibrillators, generators, neurostimulators, ventricular access devices, infusion pumps, devices for delivery of medication and hydration solutions, intrathecal delivery systems, pain pumps, and other devices to provide drugs or electrical stimulation to a body part.

B. Mesh Products

The discovery that fibers of PBS and copolymers thereof can be prepared with high initial tensile strengths, and a prolonged strength retention, has made it possible to develop mesh implants in particular for use in surgical procedures requiring prolonged strength retention. Notably, the fibers may be prepared with suitable properties for forming surgical meshes.

As discussed above, it has been discovered that fibers of PBS and copolymers thereof can be prepared that do not degrade in the first 4 weeks, preferably the first 12 weeks, by surface erosion, which can cause pitting of the surfaces of the fibers. Pitting of fibers is detrimental to the burst strength of a mesh formed from fibers, particularly when the diameters of the fibers are small. The absence of pitting makes it possible to produce meshes of PBS and copolymers thereof with more predictable rates of degradation.

It has also been discovered that meshes can be formed from PBS and copolymers thereof that have improved dimensional stability after implantation. As shown in Example 15 and Table 8, meshes comprising PBS and copolymers thereof remain dimensionally stable following implantation for at least 4 weeks, and more preferably for at least 12 weeks. This is a surprising result in view of comparative data obtained for a mesh made from a different material shown in Table 9. The finding is particularly significant when the mesh is used in procedures where it is undesirable for the mesh to shrink and place additional tension on the mesh. Thus, mesh derived from PBS and copolymers thereof, preferably comprising monofilament or multifilament oriented fibers, and preferably knit or woven mesh, is particularly suitable for use in procedures such as hernia repair, breast reconstruction, mastopexy, tissue lifting, treatment of stress urinary incontinence, pelvic organ prolapse repair, and pelvic floor reconstruction. Porous meshes comprising PBS and copolymers thereof are particularly suitable for applications where it is desirable to obtain tissue in-growth, such as in hernia repair, breast reconstruction, treatment of stress urinary incontinence with slings, and pelvic floor reconstruction or repair.

It has also been discovered that meshes made from PBS and copolymers thereof do not curl after implantation in vivo. This is another improvement since it prevents curled edges from potentially damaging nearby tissues.

In one embodiment, mesh products may be produced from the high tenacity yarns and high tensile strength monofilaments of poly(butylene succinate) and copolymers thereof, for example, by warp or weft knitting processes. In a particularly preferred embodiment, the high strength monofilament fibers of poly(butylene succinate) and copolymers thereof can be knitted or woven to make mesh products. In one embodiment, monofilament knitted mesh can be prepared using the following procedure. Forty-nine (49) spools of high strength poly(butylene succinate) or copolymer thereof monofilament is mounted on a creel, aligned side by side and pulled under uniform tension to the upper surface of a "kiss" roller. The "kiss" roller is spinning while semi-immersed in a bath filled with a 10% solution of polyethylene glycol sorbitan monolaurate, polyethylene glycol, or other suitable lubricant. The lubricant is deposited on the surface of the sheet of fiber. Following the application of the lubricant, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scoring. The poly(butylene succinate) or copolymer thereof monofilament mesh is then scoured ultrasonically with water, and may be (i) heat set (for example in a hot conductive liquid bath or an oven), and then (ii) washed with a 70% aqueous ethanol solution.

In an embodiment, the meshes made from monofilaments, multifilaments, or combinations thereof, of poly(butylene succinate) or copolymers thereof have one or more of the following properties: (i) a suture pullout strength of at least 10 N, or at least 20 N, (ii) a burst strength of 0.1 to 100 kgf, more preferably between 1 to 50 kgf, or greater than 0.1 kPa, (iii) a thickness of 0.05-5 mm, (iv) an areal density of 5 to 800 g/m$^2$, (v) pore diameter of 5 μm to 5 mm, or more preferably 100 μm to 1 mm, (vi) Taber stiffness of at least 0.01 Taber Stiffness units, more preferably 0.1-19 Taber Stiffness units, (vii) a degradation rate in phosphate buffered saline at 37° C. wherein the weight average molecular weight of the mesh decreases between 10% and 30% over a 12-week time period, and (viii) a degradation rate in vivo under physiological conditions wherein the burst strength of the mesh decreases less than 20% at 4 weeks, or wherein the burst strength of the mesh decreases less than 35% at 12 weeks. In a preferred embodiment, the monofilament or multifilament meshes have one or more of the following properties: (i) a suture pullout strength of 1 kgf to 20 kgf, (ii) a burst strength of 1 to 50 kgf, more preferably 5 to 30 kgf, (iii) a thickness of 0.1 to 1 mm, (iv) areal density of 100 to 300 g/m$^2$, and (v) pore diameter 100 μm to 1 mm. In another preferred embodiment, the monofilament or multifilament mesh of poly(butylene succinate) or copolymer thereof has substantially one or more of the following properties: a pore diameter of 500±100 µm, thickness of 0.4±0.3 mm, areal density of approx. 182±50 g/m², suture pullout strength of 5.6±2 kgf, and a burst strength of at least 3 kgf, and more preferably at least 6 kgf.

In one embodiment, the mesh can be combined with an anti-adhesion coating or film on one surface to make an implant. For example, the mesh may be coated on one side using a hydrogel barrier, such as the Sepra® coating, or using another hyaluronic acid coating. A particularly preferred mesh comprises oriented monofilament fibers of PBS or copolymer thereof coated on one side of the mesh with an anti-adhesion coating or film. Meshes coated with anti-adhesion coatings or films are particularly useful in hernia repair procedures to prevent adhesions to the visceral organs.

In another embodiment, the meshes of poly(butylene succinate) or copolymers thereof may comprise different sized fibers or other non-poly(butylene succinate) or copolymer thereof fibers, including multifilament, and fibers made from other absorbable or non-absorbable biocompatible polymers and hybrid meshes. Such meshes may be designed so that their fibers degrade at different rates in vivo.

Meshes comprising poly(butylene succinate) and copolymers thereof prepared as described herein may have a two-dimensional shape, including a polygon shape, including rectangular, square, triangle, and diamond shapes, a curved shape, including circular, semicircle, elliptical, and crescent shapes.

In yet another embodiment, the meshes described herein may be used to prepare three-dimensional implants, for example, implants that can be used in breast reconstruction, mastopexy, hernia repair, or in void filling. The three-dimensional shapes include cone, dome, partial dome, canoe, hemisphere, plug, and hemi-ellipsoid shapes. In one embodiment, these three-dimensional implants have shape memory that can be used to contour to the shape of an anatomical structure, or be used to confer shape to the patient's tissue. For example, these three-dimensional implants can be used in mastopexy and breast reconstruction procedures to confer shape to the host's breast tissue or form an anatomical shape of the breast. In one embodiment, these three-dimensional implants have shape memory that allows them to resume their three-dimension shape after delivery into the body (such as laparoscopic delivery), for example, through a trocar or similar delivery device. These three-dimensional implants can be used for laparoscopic inguinal hernia repair wherein the implant has a three-dimensional shape suitable to conform to the inguinal anatomy, and retain its shape following laparoscopic introduction. Suitable three-dimensional implants of poly(butylene succinate) and copolymers thereof may be manufactured by molding a two-dimensional monofilament mesh made from poly(butylene succinate) and copolymers thereof. In one process, the mesh may be molded using a split metal form consisting on an inwardly curving half and a mating outwardly curving half. The three-dimensional implant may be formed by draping the mesh over the inwardly curving half of the metal form, placing the outwardly curving half of the metal form other the mesh, clamping the split metal form together to form a block, and heating the block to mold the mesh. In another process, the three-dimensional implants may be plugs, preferably hernia plugs, made from meshes of poly(butylene succinate) and copolymers thereof.

In another embodiment, the three-dimensional implants comprising poly(butylene succinate) and copolymers thereof maybe implanted in the breast, preferably instead of breast implants. In a particularly preferred embodiment, the three-dimensional implants comprise pleats, chambers or compartments. Preferably the pleats, chambers and compartments are made with monofilament fibers of poly(butylene succinate) and copolymers thereof. The chambers or compartments may be filled with tissues during implantation, for example, the chambers or compartments may be filled with one or more of the following: cells, including stem cells, protein, including collagen, fat and fascia. In a particularly preferred embodiment, the three-dimensional implants may have the shape of a lotus flower or a funnel shape. In an even more preferred embodiment, the three-dimensional implants may have the shape of a lotus flower or funnel shape, and are made from monofilament fibers of poly(butylene succinate) or copolymer thereof.

Meshes comprising poly(butylene succinate) or copolymer thereof may also be prepared that are expandable. These meshes can be prepared so that the fibers of the meshes stretch or elongate so that the meshes can expand. The meshes may comprise fibers of poly(butylene succinate) or copolymer thereof that are unoriented, partially oriented or fully oriented. The meshes may also be designed to expand without the fibers of the meshes stretching. In one embodiment, the meshes may have a knit pattern that provides the mesh with the ability to stretch under force. For example, the mesh may comprise pores that can elongate under force, or loops that can shorten as force is applied. In another embodiment, the meshes may comprise a combination of stronger and weaker fibers, wherein the weaker fibers break when a force is applied allowing the meshes to stretch. Expandable meshes comprising poly(butylene succinate) or copolymer thereof are particularly suitable for use in breast reconstruction, more particularly in combination with the use of a tissue expander. The expandable meshes preferably comprise monofilament fibers made from poly(butylene succinate) and copolymers thereof.

In a further embodiment, the meshes described herein may further comprise barbs, hooks, self-anchoring tips, micro-grips, fleece, reinforcement, and a reinforced outer edge or border.

In another embodiment, non-woven meshes may be prepared from the high tenacity yarns by entangling fibers using mechanical methods. The properties of the nonwovens can be tailored by selection of parameters such as fiber diameter, fiber orientation, and length of the fibers (for staple nonwovens). In a preferred embodiment, the non-woven meshes prepared from the high tenacity yarns have one or more of the following properties (i) a thickness of 0.1-5 mm, (ii) an areal density of 5 to 800 g/m², (iii) a suture pullout strength of greater than 10 N, and (iv) a burst strength that is able to withstand a pressure of at least 0.1 kPa.

In another embodiment of the invention, the high tenacity yarns of poly(butylene succinate) and copolymers thereof, may be knit to produce circular knits. Circular knits comprising the high tenacity yarns may be used, for example, as vascular grafts. In one embodiment, a circular knit of the high tenacity yarns of poly(butylene succinate) and copolymers thereof may be produced using a single feed, circular weft knitting machine (Lamb Knitting Co., model ST3A/ZA).

In another preferred embodiment of the invention, it has been discovered that implantable meshes may also be formed by 3D printing. These meshes are particularly suitable for use in breast reconstruction, hernia repair, pelvic floor reconstruction and treatment of stress urinary incontinence using slings. Two different methods of 3D printing poly(butylene succinate) and copolymers thereof are described in Examples 9 and 10. FIG. 1 shows an image of a mesh that was 3D printed according to the method of Example 9. The high quality of the mesh is apparent from the image. The method is particularly suitable for forming three-dimensional mesh implants comprising PBS and copolymers thereof, including, for example, hernia plugs, and meshes with three-dimensional shapes that are designed to contour to the patient's anatomy. The method may also be used to prepare 3D meshes of PBS and copolymers thereof for breast reconstruction, include breast implants, expandable meshes, and full contour implants. In an embodiment, the 3D printed mesh implants comprising PBS or copolymers thereof have one or more of the following properties: burst strength of 1 kgf to 25 kgf, and more preferably 3 kgf to 10 kgf; thickness of 50 µm to 3 mm, and more preferably 100 µm to 800 µm; pore size between 75 µm and 5 mm; a total porosity of at least 50%, but less than 100%, and a weight average molecular weight of 25 kDa to 500 kDa, and more preferably 50 kDa to 300 kDa by GPC relative to polystyrene.

The meshes comprising PBS and copolymers thereof disclosed herein may be used in the following implants: wound closure device, patch, wound healing device, device for tissue or suture line reinforcement, tracheal reconstruction device, organ salvage device, dural patch or substitute, nerve regeneration or repair device, hernia repair device, hernia mesh, hernia plug, inguinal hernia plug, device for temporary wound or tissue support, tissue engineering scaffold, guided tissue repair/regeneration device, anti-adhesion membrane or barrier, tissue separation membrane, retention membrane, sling, device for pelvic floor reconstruction, urethral suspension device, device for treatment of urinary incontinence, bladder repair device, void filling device, bone marrow scaffold, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, cardiovascular patch, vascular closure device, intracardiac septal defect repair device, atrial septal defect repair device, patent foramen ovale closure device, left atrial appendage closure device, pericardial patch, vascular graft, myocardial regeneration device, periodontal mesh, guided tissue regeneration membrane for periodontal tissue, imaging device, anastomosis device, cell seeded device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, rhinoplasty device, device for malar augmentation, otoplasty device, neck lift device, mentoplasty device, buttock lift device, cosmetic repair device, device for facial scar revision, a pouch, holder, cover, enclosure, or casing to partially or fully encase, surround or hold an implantable medical device, a cardiac rhythm management device, a pacemaker, a defibrillator, a generator, an implantable access system, a neurostimulator, a ventricular access device, an infusion pump, a device for delivery of medication and hydration solution, an intrathecal delivery system, a pain pump, or device that provides drug(s) or electrical stimulation to the body.

C. Orthopedic Implants

In an embodiment, orthopedic implants may be prepared from polymeric compositions comprising poly(butylene succinate) and copolymers thereof. Optionally, these implants may comprise a ceramic or bioceramic. In one embodiment, implants may be formed from poly(butylene succinate) and copolymers thereof, optionally with ceramic present, that include screws, pins, ACL screws, clips, clamps, nails, medullary cavity nails, bone plates, tacks, fasteners, rivets, staples, fixation devices, bone void fillers, suture anchors, bone anchors, osteochondral repair devices, spinal fusion devices, and device for treatment of osteoarthritis. It has been discovered that implants can be made from the compositions of poly(butylene succinate) and copolymers thereof with high stiffness and torsional strength making the implants suitable for use in orthopedic implants.

In one embodiment, the orthopedic implants may be produced by injection molding. For example, injection molded implants of PBS and copolymers thereof may be formed using an Arburg model 221 injection molder using the following conditions: barrel temperature of the molder increasing from 70° C. at the feed zone to 170° C. at the end of the barrel; and mold temperature of 32° C. After molding, the implants may be dried in a vacuum oven at room temperature for 48 hours, and tensile properties determined using an MTS test machine with a 2 inch/min cross head speed. Representative tensile properties of implants formed by this method are as follows: Young's Modulus 0.66 GPa (96,600 psi), Yield Strength 49.2 MPa (7,140 psi) and Break Stress of 71.7 MPa (10,400 psi). Example 8 discloses the manufacture of an interference screw by injection molding. The torsional strength of screws made from PBS and copolymer thereof is preferably between 10 Ncm and 18 Ncm. This strength may be further increased by blending the polymeric compositions with a ceramic prior to injection molding. A suitable ceramic is tri-calcium phosphate. Suitable blend ratios are 10-50 wt. % of the ceramic. Interference screws prepared with the bioceramic may have torsional strengths of at least 10-20 Ncm, as is disclosed in Example 8.

D. Other Implants

In an embodiment, absorbable stents may be prepared from poly(butylene succinate) or copolymers thereof by first producing a tubular stent blank. Tubes may be prepared by melt extrusion, injection molding, solvent dipping, or similar processes that yield a tube with consistent wall thickness of approximately 0.001 to 0.500 mm. The stent structure may be cut into the blank using mechanical or laser processes to remove material from selected areas of the tube blank. The stent may be delivered to a location of the body and deployed by balloon expansion, or removed from a sheath in the body and allowed to self-deploy if the stent is self-expanding. The stent structure provides support to the adjacent tissue and/or delivers therapeutic agents that may be included in the stent material or coated onto its surface.

In another embodiment, microbeads may be prepared from poly(butylene succinate) or copolymers thereof using solvent techniques or melt processing approaches. The microbeads may contain a therapeutic agent and may deliver that agent to the tissue after injection into the tissue. The beads may also be used to occlude a blood vessel or provide additional volume to the tissue.

In a further embodiment, staple line reinforcement material may be prepared from the poly(butylene succinate) or copolymers thereof using methods to prepare medical textiles such as knitting, weaving, or non-woven processes. Alternatively, the staple line reinforcement materials may be produced from porous foams of poly(butylene succinate) or copolymers thereof. The staple line reinforcing material may be used to provide a backing material to weakened or friable tissue that could not reliably support a surgical staple or suture. In this way, the staple line reinforcement material may also function as a pledget or backing material for a surgical suture. Additionally, the staple line reinforcing material may also be used to seal a tissue and prevent leakage of air, blood or other body fluids during a surgical repair. This can facilitate a procedure allowing a surgeon to more quickly, consistently and reliably make a surgical resection, staple line reinforcing material repair, or anastomosis to tissues such as the lungs, blood vessels, bowel or similar tissues.

In another embodiment, absorbable clips for tissue ligation may be prepared from poly(butylene succinate) or copolymers thereof using melt processing techniques such as injection molding or 3D printing. The absorbable clips may be used when a permanent clip is not desired or to treat a temporary condition. Absorbable clips or cuffs may be useful to prevent or stop bleeding, to restrict flow of material or liquid through a vessel. Bariatric clips or cuffs may be preferred for treating obesity or eating disorders and may be preferred over permanent, invasive surgeries.

In yet another embodiment, absorbable filters to trap blood clots may be prepared from the poly(butylene succinate) or copolymers thereof. Such vena cava filters may be preferred over permanent metal or polymer filters as they could obviate the need for a second procedure to remove the filter after the need for the filter has passed.

V. Methods of Delivering Implants Made from POLY(BUTYLENE SUCCINATE) and Copolymers Thereof The implants made from poly(butylene succinate) and copolymers thereof may be implanted using conventional open surgical techniques, but may also be implanted using minimally invasive techniques. In one embodiment, high strength sutures are implanted using arthroscopic techniques. In a particularly preferred embodiment, the high strength sutures and suture tapes are used for arthroscopic repair of shoulders, elbows, wrists, spine, hips, knees, ankles and feet, including ligament and tendon repair. In another embodiment, meshes, webs, and lattices made from high strength monofilaments and high tenacity yarns, or by 3D printing of poly(butylene succinate) and copolymers thereof may be implanted using laparoscopic techniques. In a preferred embodiment, meshes, webs and lattices are implanted for the repair of hernias, and lift procedures, using laparoscopic techniques and other minimally invasive techniques.

In a particularly preferred embodiment, the implants may be used in any current mastopexy technique to achieve a breast lift using any appropriate skin resection pattern. The chosen method will depend upon the extent of breast ptosis and a number of other factors. The four main techniques for mastopexy are the: crescent mastopexy, donut (or Benelli) mastopexy, lollipop (or vertical) mastopexy, and anchor (or Weiss or Wise) mastopexy. In the crescent mastopexy, a semi-circular incision is made on the upper side of the areolar, and a crescent shaped piece of breast tissue removed. This procedure is typically used for patients with only mild ptosis where a good lift can be achieved by removing excess skin on the upper breast, and suturing the skin back in order to elevate the areolar nipple complex. In one embodiment, the implants can be implanted after further dissection and/or resection to provide additional support for the upper breast tissue.

The implants can also be implanted during a donut or Benelli mastopexy. In this procedure, a donut shaped piece of breast skin is removed from around the areolar with an inner incision line following the perimeter of the areolar, and an outer incision line circling the areolar further out. In one embodiment, the implant(s) can be inserted after further dissection to support the lift, and a purse string suture used to approximate the breast skin back to the areolar.

In both the lollipop and anchor mastopexy procedures, incisions are made around the areolar complex. In the lollipop procedure, a vertical incision is made in the lower breast from the areolar to the inframammary fold, and in the anchor mastopexy procedure an incision is made across the inframammary fold in addition to the vertical incision used in the lollipop procedure. The lollipop procedure is generally used for patients with moderate ptosis, whereas the anchor procedure is normally reserved for patients with more severe ptosis. These two procedures can be performed with or without breast implant augmentation. In both procedures, breast tissue may be resected, and the resected edges sutured together to create a lift. Prior to suturing the resected tissue, the implants can be implanted to support the breast, and to decrease the forces on the resected skin and suture line after closure. In a particularly preferred procedure, the implants are positioned to support the breast parenchyma or implant, and to minimize the weight of the breast on the skin and suture line. In an even more preferred procedure, the suture line is closed with minimal or no tension on the wound to minimize scar formation.

In a preferred embodiment, when sutured in place, the implants provide support, elevation and shape to the breast by anchoring of the implants at one or more locations to the tissue, muscle, fascia or the bones of the chest or torso. In a particularly preferred embodiment, the implants are sutured to the pectoralis fascia or the clavicle. The implants may also be sutured to the chest wall or fascia, and in a particularly preferred embodiment, the implants may be sutured to the chest wall so that they provide slings for support of the lifted breast or breast implant.

Modifications and variations of the invention described herein will be obvious to those skilled in the art and are intended to come within the scope of the appended claims.

The present invention will be further understood by reference to the following non-limiting examples.

EXAMPLES

Example 1: Monofilament Melt Extrusion of Succinic acid-1,4-Butanediol-Malic acid Copolyester with Two Stage Orientation in Convective Chambers to Produce Monofilament Fiber for Implants Succinic acid-1,4-butanediol-malic acid copolyester (Tepha lot 180333) with weight average molecular weight of 184 kDa, Tm=115° C., (melt flow rate (MFR) at 190° C./2.16 kgf of 5 g/10 min) was dried under vacuum overnight to less than 0.01% (w/w) water. Dried pellets of the polymer were fed into an extruder barrel of an AJA (Alex James Associates, Greer, South Carolina) ¾ single screw extruder (24:1 L:D, 3:1 compression) equipped with a Zenith type metering pump (0.16 cc/rev) and a die with a single hole spinneret (0.026", 2:1 L:D) under a blanket of nitrogen. The 4 heating zones of the extruder were set at 75° C., 165° C., 180° C. and 180° C. The extruder was fitted with a quench bath filled with water at 35° C. and set up with an air gap of 10 mm between the bottom of the spinneret and the surface of the water. Two 2-roll godets were positioned after the quench bath, followed by two sets of longitudinal hot convection chamber/2-roll godet combination. The temperatures of the hot convection chambers were set between 60° to 80° C., followed by 2-roll godets then a horizontal winder. Pellets of the copolyester were allowed to enter the heated extruder barrel, molten polymer passed through the barrel, entered a heated block followed by a metering pump then a single hole spinneret. The block, metering pump and the spinneret die were maintained at a constant temperature, preferably 180° C. Pump discharge pressure was kept below 1500 psi by controlling the temperatures and the speed of the metering pump. The resulting spun extrudate filament was free from all melt irregularities. The extrudate was quenched in a water bath, drawn through longitudinal ovens and wound on a horizontal tension controlled Sahm winder. The results of 3 trials with in-line orientation and shown in Table 1, together with the result of a fourth trial where the fiber was not oriented in-line, but rather off-line and 10 days after it had been extruded. From inspection of Table 1, it will be evident that the conditions used to prepare the monofilament fiber resulted in fiber with a tensile strength in the range of 434-518 MPa.

TABLE 1

Properties of monofilament fibers made from PBS copolymer derived from 2-stage orientation in convention ovens

| Trial | #1 | #2 | #3 | #4 |
|---|---|---|---|---|
| Orientation | Online | Online | Online | Offline |
| Delay | None | None | None | 10 days |
| Godet 1 (m/min) | 3.3 | 3.3 | 3.3 | 3.3 |
| Hot Chamber 1 (° C.) | 62 | 62 | 70 | 70 |
| Godet 2 (m/min) | 18.6 | 18.6 | 18.5 | 15 |
| Hot Chamber 2 (° C.) | 75 | 75 | 80 | 80 |
| Godet 3 (m/min) | 22 | 21 | 23 | 22.5 |
| Orientation ratio (total) | 6.67 | 6.36 | 6.97 | 6.82 |
| Fiber Diameter (mm) | 0.178 | 0.182 | 0.183 | 0.172 |
| Tensile Strength (MPa) | 452 | 449 | 434 | 518 |
| Break Elongation (%) | 46 | 67 | 41 | 24 |

Example 2: Monofilament Melt Extrusion of Succinic Acid-1,4-Butanediol-Malic Acid Copolyester with Multi Stage Incremental Orientation in Conductive Chambers to Produce Monofilament Fiber for Implants Succinic acid-1,4-butanediol-malic acid copolyester (Tepha lot 180333) with weight average molecular weight of 184 kDa, $P_D$=2.83, Tm=115° C., (MFR 190° C., 2.16 kg, 5 g/10 min) was dried under vacuum overnight to less than 0.01% (w/w) water. Dried pellets of the polymer were fed under a blanket of nitrogen into the extruder barrel of a 2½" American Kuhne single screw extruder (30:1 L:D, 3:1 compression) equipped with a Zenith type metering pump model HPB917, a die with 0.5 mm-8 hole spinneret and 8 heat zones. The 8 heating zones of the extruder were set between 40° C. and 200° C. The extruder was fitted with a quench bath filled with water at 35°-70° C. and set up with an air gap of 10 mm between the bottom of the spinneret and the surface of the water. Two 5-roll godets were positioned after the quench bath, followed by three sets of hot conduction chambers fed by godets in order to orient the fiber in multiple stages. The temperatures of the hot chambers were set up between 50° to 90° C. temperature. Another godet was positioned after the last chamber, and then a multi-position Sahm winder. The results from three trials are shown in Table 2. In comparison to the results shown in Table 1, the use of multi-stage incremental orientation of the fiber and conductive chambers instead of standard conventional non-liquid chambers resulted in monofilament fiber with substantially higher tensile strengths of 779-883 MPa.

TABLE 2

Properties of monofilament fibers made from PBS copolymer derived from multi-stage orientation in conductive liquid chambers

| Trial | #1 | #2 | #3 |
|---|---|---|---|
| Orientation | Online | Online | Online |
| Godet 1&2 (m/min) | 3.6 | 3.6 | 1 |
| Hot Chamber 1 (° C.) | 55 | 55 | 60 |
| Godet 3 (m/min) | 14 | 14 | 3.7 |
| Hot Chamber 2 (° C.) | 80 | 80 | 65 |
| Godet 4 (m/min) | 28 | 28.3 | 7.7 |
| Hot Chamber 3 (° C.) | 85 | 85 | 65 |
| Godet 5 (m/min) | 30 | 29.7 | 8.22 |
| Orientation Ratio | 8.3 | 8.25 | 8.2 |
| Diameter (mm) | 0.169 | 0.166 | 0.167 |
| Tensile Strength (MPa) | 779 | 752 | 883 |
| Break Elongation (%) | 24 | 23.7 | 23 |
| Young's Modulus (GPa) | 2.8 | n.d. | n.d. |

Example 3: Multifilament extrusion of Succinic acid-1,4-Butanediol-Malic acid Copolyester to Prepare Implants Succinic acid-1,4-butanediol-malic acid copolyester (Tepha lot 180333) with weight average molecular weight of 184 kDa, $P_D$=2.83, Tm=115° C., (melt flow rate (MFR) at 190° C./2.16 kgf of 5 g/10 min), was dried under vacuum overnight to less than 0.01% (w/w) water. Dried pellets of the polymer were fed into an extruder barrel of an AJA (Alex James Associates, Greer, South Carolina) ¾" single screw extruder (24:1 L:D). The extrusion barrel contained 4 heating zones, a metering pump and a spin pack assembly. The pellets were gravity fed into a chilled feeder section and introduced into the extruder with temperature profile set as follows: Chimney 40° C.-100° C., Spinneret 170° C.±30° C., Pump 170° C.±30° C., Block 170° C.±30° C., Zone 4 160° C.±40° C., Zone 3 150° C.±40° C., Zone 2 120° C.±50° C., Zone 1 30° C.-40° C., Feed Zone: Ambient temperature. The heated and homogenized melted resin from the extruder was fed into a heated metering pump (melt pump), and from the melt pump the extruded resin was fed into the heated block and the spinneret assembly. The spinneret had 30 holes with a capillary diameter of 0.200 millimeters and a L/D ratio of 2:1. (The spinneret may also be configured in other alternative manners. For example, the spinneret can be configured with capillary diameters from 0.150 to 0.300 millimeters and 15, 120 and 240 holes, as well as higher and lower diameters and numbers of holes.) Processing temperature profile ranges from 35° C. to 250° C. were used with pressures ranging from 200 to 5,000 psi in the barrel and 200 to 5,000 psi in the spin pack. As the molten filaments exited the spin pack they passed through a heated chimney collar that was 6-12 inches long and ranged in temperature from 40° C. to 100° C., and then through an air quench box. The spin pack was suspended vertically above a yarn take-up roll at a distance sufficient to allow crystallization of the molten filaments and application of spin finish lubricant. A spin finish solution of 25% polyethylene 25 glycol 400 (PEG400) in water was used to hold the filaments together to form a yarn bundle. The speed of the yarn take-up rolls (typically 3-18 meters per minute) was set in proportion to the flow rate of the molten filament to control the denier of the as spun yarn bundle. The as spun yarn bundle was then conveyed to a Lessona winder for offline later orientation or conveyed to a take-up roll for inline orientation on a series of cold and heated godet pairs and separator rolls. The spin finish can be reactivated by rewetting the yarn bundle with pure water, and the yarn drawn at ratios from 5 to 14× and temperatures ranging from 50° C. to 90° C. The tenacity and denier of the multifilament yarn produced is shown in Table 3.

TABLE 3

Properties of Multifilament Fibers made from PBS Copolymer Prepared by Melt Extrusion

| Number of Filaments | Denier | Load (Kg) | Break Elongation (%) | Tenacity (gpd) |
|---|---|---|---|---|
| 15 | 60 ± 10 | 0.50 ± 0.05 | 16% | 8.3 |
| 30 | 63 ± 10 | 0.79 ± 0.04 | 20% | 12.5 |
| 30 | 152 ± 10 | 1.55 ± 0.07 | 21% | 10.2 |
| 60 | 309 ± 10 | 2.80 ± 0.10 | 24% | 9.1 |

Example 4: Preparation of Multifilament Sutures

Oriented yarn produced according to Example 3 and with properties shown in Table 3 was braided using 8 and 16 carrier Steeger braiding equipment to form the braid constructions shown in Table 4. The mechanical properties of the high strength braided sutures, determined according to USP 24, are also shown in Table 4. The examples include a braid formed as a tape (shown as the last example in Table 4.

TABLE 4

Mechanical Properties of Braids and Tapes Prepared from PBS Copolyester

| | Braid Construction | | | | Mechanical Properties | |
|---|---|---|---|---|---|---|
| Lot Number | Core denier | Sheath denier | Pick count | Diameter (mm) | Tensile strength, (Kg) | Break elongation (%) |
| TE18-008 | 2 × 152 | 16 × 152 | 48 | 0.608 | 26.5 | 39 |
| TE18-010 | 3 × 63 | 16 × 63 | 58 | 0.380 | 14.2 | 31 |
| TE18-010 | 1 × 60 | 8 × 60 | 49 | 0.246 | 4.3 | 26 |
| TE18-021 Tape Suture | | 13 × 6 × 126 denier | 17 | 0.5 × 3.0* | 62 | 40 |

*Tape dimensions of 0.5 mm thickness and 3.0 mm width

Example 5: Preparation of a Knitted Monofilament Mesh Implants

Monofilament fiber (USP suture size 5/0) prepared according to the method of Example 2 was processed into knitted mesh according to the following procedure. Monofilament fibers from 49 spools were mounted on a creel, aligned side by side and pulled under uniform tension to the upper surface of a "kiss" 10" roller. The "kiss" roller was spun while semi-immersed in a bath filled with a 10% solution of TWEEN® 20 lubricant. The TWEEN® 20 lubricant was deposited on the surface of the sheet of monofilament fibers. Following the application of TWEEN® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of 20 dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll and scored ultrasonically with water, heat set in hot water, and then washed with a 70% aqueous ethanol solution. The knitted mesh produced with monofilament fiber from Example 2 had the following properties (as shown in Table 11 at time 0): burst strength of 22.668 kgf, thickness of 0.683 mm, and Taber Stiffness of 0.116.

Example 6: Preparation of Knitted Multifilament Mesh Implants

Spools of multifilament fiber prepared according to the method of Example 3 were processed into knitted multifilament mesh using the method described in Example 5.

Example 7: Injection Molded Implants

Injection molded implants of succinic acid-1,4-butanediol-malic acid copolyester (Tepha lot 180333) with weight average molecular weight of 184 kDa, Tm=115° C., were prepared using an Arburg model 221 injection molder using the following conditions. The barrel temperature of the molder was increased from 70° C. at the feed zone to 170° C. at the end of the barrel. The mold temperature was maintained at 32° C. After molding, the implants were dried in a vacuum oven at room temperature for 48 hours, and tensile properties determined using an MTS test machine with a 2 inch/min cross head speed. Representative tensile properties of the implants were as follows: Young's Modulus 0.66 GPa (96,600 psi), Yield Strength 49.2 MPa (7,140 psi) and Break Stress of 71.7 MPa (10,400 psi).

Example 8: Injection Molded Interference Screws for Use as Implants

Interference screws with a diameter of 7 mm and length of 20 mm were injection molded from succinic acid-1,4-butanediol-malic acid copolyester (Tepha lot 180333), and from the same copolyester after blending with 50 wt. % beta-TCP (tri-calcium phosphate). The screws were formed using a similar procedure to that described in Example 7. After injection molding of the screws, the intrinsic viscosity of the compositions was essentially identical to that of the starting materials, indicating little loss of weight average molecular weight during injection molding occurred. The torsional strength of the screws was determined by embedding the tip of the molded screws in epoxy resin and measuring the maximum torque achieved by the screwdriver before failure of the screws. The average of three screws tested for the copolyester alone gave a value for torsional strength of 15.0 Ncm. The testing was repeated for the screws prepared from the blend, and the average value was 18.2 Ncm. For comparison, a commercial Arthrex Biointerference screw for implantation composed of PLLA (poly-L-lactic acid) was also tested. The Arthrex Biointerference screw has an average failure torque of 12.1 Ncm.

Example 9: 3D Printed Implantable Mesh

A 3D printed mesh was prepared from succinic acid-1,4-butanediol-malic acid copolyester (Tepha lot 180333), with weight average molecular weight of 184 kDa, Tm=115° C., using melt extrusion deposition according to the following method. The mesh was printed using an ARBURG Free-Former machine consisting of a horizontal extruder feeding into a vertical ram extruder fitted with motion controlled needle plunger, 200 micron spinneret nozzle and a movable stage table. The extruder hopper was charged with 1½×3 mm sized polymer pellets with a moisture content of less than 2,000 ppm. The pellets were purged with dry nitrogen in the extruder hopper to maintain dryness. The temperature profile of the extruder was set between 45°-180° C., and the residence time of the polymer in the extrusion system was maintained at less than 15 min/cm. The conditions resulted in the formation of very high quality printed mesh as shown in FIG. 1.

Example 10: 3D Printed Implantable Lattice

A 3D printed lattice was prepared from succinic acid-1,4-butanediol-malic acid copolyester (Tepha lot 180333), with weight average molecular weight of 184 kDa, Tm=115° C., using selective laser melting (SLM). The SLM equipment consisted of a moving powder bed equipped with a reservoir for the polymer granules and a powder sweeper gate valve, and a laser source that can direct a laser beam on the powder bed and focus on a single polymer granule in the bed. The position of both the moving powder bed and laser beam were controlled by a computer that had been programmed with 3D CAD data to produce a lattice structure of the copolyester. The powder bed could be moved in the X-Y horizontal plane, and also in the Z axis vertical plane. The focal distance, the distance between the lens and surface of the powder was less than 50 cm. Prior to printing, the polymer was cryo-milled using liquid nitrogen, and sieved to produce granules with average sizes of 0.3 to 250 μm. The granules were placed in the powder reservoir, and a first layer of powder, 250 μm thick, was spread on the moving bed using the powder sweeper. The computer driven laser beam was focused on each polymer granule until it melted, shifting from one granule when it melted to the next granule. After printing of the first layer, a sweeper arm spread a second layer of polymer granules, the laser position was adjusted to focus on the granules, and laser firing started to form the second 3D layer. The process was repeated with successive layers until the lattice made of succinic acid-1,4-butanediol-malic acid copolyester was formed.

Example 11: Endotoxin Testing of Copolymer of Succinic Acid and 1,4-Butanediol

Polymer pellets of succinic acid-1,4-butanediol-malic acid copolyester were tested for endotoxin content using the Bacterial Endotoxin Test (BET) Gel Clot method per USP<85>. Before testing, the pellets were sterilized by exposure to ethylene oxide gas. The extraction was performed at a ratio of 1 gram of polymer in 10 mL of endotoxin-free water; then, a 1:8 dilution of the sample extract was prepared and tested by the gel clot method. The results yielded<2.5 EU/g of polymer.

Example 12: In Vitro Degradation of an Implantable Mesh Prepared from Succinic Acid-1,4-Butanediol-Malic Acid Copolyester The in vitro degradation rate of an implantable mesh prepared from oriented monofilament fibers of succinic acid-1,4-butanediol-malic acid copolyester (prepared as described in Example 5) was studied by incubation of the mesh in phosphate buffered saline. The buffer solution contained 137 mM NaCl, 2.7 mM KCl, 9.8 mM phosphate and 0.05 wt % sodium azide and had pH 7.4 at 25° C. The prepared buffer solution was filtered through a 0.45 um filter (VWR Product # 10040-470) prior to use. Mesh samples were sterilized by exposure to ethylene oxide gas. Samples (2×2 in.) were placed in sterile containers covered in buffer solution and incubated in a shaker incubator at 50 rpm and at a temperature of 37° C. Buffer media was monitored monthly and changed if the pH was outside of the targeted value 7.4±0.2. At prescribed time points, the samples were removed from the buffer and rinsed with deionized water to remove buffer salts. The samples were then tested for mechanical properties and weight average molecular weight retention of the polymer by gel permeation chromatography (as further described in Example 15). The in vitro degradation data is shown in Table 5.

TABLE 5

Mechanical and Mw data for PBS mesh samples made from oriented PBS monofilament fiber after incubation in phosphate buffered saline (pH 7.4) at 37° C.

| Time point (weeks) | Thick (mm) | Peak Load (kgf) | Std Dev (kgf) | Strength Retention (%) | Mw (kDa) | Std Dev (Daltons) | Poly-dispersity | Mw Retention (%) |
|---|---|---|---|---|---|---|---|---|
| 0 | 0.696 | 21.773 | 1.034 | 100.0 | 174 | 0.9 | 5.26 | 100.0 |
| 2 | 0.689 | 21.117 | 1.566 | 97.0 | 166 | 0.2 | 5.08 | 95.4 |
| 4 | 0.696 | 19.923 | 1.141 | 91.5 | 160 | 0.2 | 4.94 | 92.1 |
| 8 | 0.692 | 19.537 | 1.135 | 89.7 | 147 | 0.7 | 4.58 | 84.2 |
| 12 | 0.709 | 18.630 | 1.044 | 85.6 | 134 | 0.8 | 4.33 | 77.2 |

Example 13: In Vitro Degradation of an Implantable Suture Prepared from Succinic acid-1,4-Butanediol-Malic acid Copolyester The degradation rate of an implantable suture prepared from oriented monofilament fibers of succinic acid-1,4-butanediol-malic acid copolyester in vitro was studied by incubation of the suture in phosphate buffered saline. The initial properties of the suture are shown in Table 6, line 1

(t=0). The buffer solution contained 137 mM NaCl, 2.7 mM KCl, 9.8 mM phosphate and 0.05 wt % sodium azide and had pH 7.4 at 25° C. The prepared buffer solution was filtered through a 0.45 um filter (VWR Product # 10040-470) prior to use. Suture samples were sterilized by exposure to ethylene oxide gas. Samples (12 in. length) were placed in sterile containers covered in buffer solution and incubated in a shaker incubator at 50 rpm and at a temperature of 37° C. Buffer media was monitored monthly and changed if the pH was outside of the targeted value 7.4±0.2. At prescribed time points, the samples were removed from the buffer and rinsed with deionized water to remove buffer salts. The samples were then tested for mechanical properties and weight average molecular weight (Mw) retention of the polymer by gel permeation chromatography (as further described in Example 15). The in vitro degradation data is shown in Table 6.

pared to a commercial mesh, the "GalaFLEX mesh (Galatea Surgical, Lexington, Massachussets)" prepared from knitting of poly-4-hydroxybutyrate monofilament in an in vivo implantation study in rabbits. The weight average molecular weight of the PBS mesh fibers prior to implantation was 173 kDa. The PBS and GalaFLEX meshes were implanted in the dorsal, subcutaneous tissue of New Zealand White rabbits to evaluate the local tissue reaction, the degree of tissue in-growth and the changes in mechanical properties of the meshes over time in vivo. Six (6) female New Zealand White (NZW) rabbits were implanted with 6 mechanical (4×4 cm), 1 histological (2×2 cm), and 1 scanning electron microscopy (SEM) (2×2 cm) test articles per animal.

Prior to implantation, the rabbits (weighing at least 3.5 kg at implantation) were anesthetized by an intramuscular injection, followed by maintenance under isoflurane. Following anesthesia, the animals were injected subcutaneously

TABLE 6

Mechanical and Mw data for oriented PBS suture samples after incubation in phosphate buffered saline (pH 7.4) at 37° C.

| Time point (weeks) | Peak Load (kgf) | Std Dev (kgf) | Break Elongation (%) | Strength Retention (%) | Mw (kDa) | Std Dev (Daltons) | Poly-dispersity | Mw Retention (%) |
|---|---|---|---|---|---|---|---|---|
| 0 | 1.793 | 0.007 | 25.133 | 100.0 | 174 | 0.2 | 4.86 | 100.0 |
| 2 | 1.801 | 0.009 | 25.120 | 100.4 | 167 | 0.8 | 4.93 | 96.2 |
| 4 | 1.810 | 0.010 | 25.364 | 100.9 | 163 | 0.5 | 4.84 | 93.6 |
| 8 | 1.772 | 0.020 | 25.311 | 98.8 | 155 | 1.5 | 5.78 | 89.4 |
| 12 | 1.736 | 0.021 | 24.866 | 96.8 | 146 | 0.6 | 4.85 | 83.1 |

Example 14: Elemental Analysis of Succinic Acid-1,4-Butanediol-Malic Acid Copolyester The elemental composition of the Succinic acid-1,4-Butanediol-Malic acid copolyester was analyzed by Proton Induced X-ray Emission (PIXE) at Elemental Analysis Inc. This method provides quantitative elemental composition of a material for inorganic elements sodium through uranium on the periodic table. The elements found are shown in Table 7. The polymer did not contain detectable heavy metals such as Tin, which is sometimes used in the manufacture of resorbable polymers such as poly-glycolide, polylactide and poly-glycolide-co-lactide. The following trace elements were detected: silicon 18.98 ppm, titanium 14.77 ppm, and zinc 5.967 ppm.

TABLE 7

PIXE Analysis of a Poly(butylene succinate) Polymer

| Element Name | Energy (keV) | Det. Limit 95% Conf. | Concentration Mass | Error |
|---|---|---|---|---|
| Silicon | 1.740 | 8.964 ppm | 18.980 ppm | 5.056 ppm |
| Titanium | 4.511 | 2.362 ppm | 14.770 ppm | 2.057 ppm |
| Zinc | 8.639 | 0.457 ppm | 5.967 ppm | 0.544 ppm |

Example 15: Comparison of In Vivo Properties of an Implantable Mesh Prepared from Succinic acid-1,4-Butanediol-Malic acid Copolyester versus an Implantable Mesh Prepared from Poly-4-hydroxybutyrate The properties of a monofilament knitted mesh prepared from a copolymer of 1,4-butanediol and succinic acid units (the "PBS" mesh), as described in Example 5, were com-with an analgesic. The surgical sites were prepared for implantation. An incision was made through the skin and the skin was resected laterally by blunt dissection to create a pocket. Three individual mechanical samples (4×4 cm) and 1 histo/SEM sample (2×2 cm) were implanted on each side of each animal, for a total of 8 specimens per animal. The specimens were implanted by placing the mesh flat along the back of the animal without folding or rolling and fixated with a Prolene suture at each corner. The skin was closed and a bandage was applied. The animals were returned to their respective cages, monitored for recovery from the anesthetic, and then monitored daily for general health.

At 4 and 12 weeks, three rabbits were euthanized from each group. The skin was reflected, the subcutaneous tissues were examined and the area around each implant was dissected free. The implanted meshes were recovered by dissection from the surrounding tissue. The explants were processed for histological, biomechanical and polymer testing. At each time point, half of the 4×4 cm implanted meshes (n=9) were tested for mechanical properties including the in-grown tissue. The other samples (n=9), were designated for mesh-only analyses and were tested following collagenase digestion to remove ingrown tissue and evaluate the residual strength of the residual polymeric scaffold. In this way, the mechanical properties of the mesh alone could be measured and compared to that of the combination of mesh and tissue in the composite.

For the mesh-only samples, the in-grown tissue was removed from the explanted samples using enzymatic digestion with collagenase. Previous testing demonstrated no impact of the collagenase enzyme on the mesh mechanical properties or Mw properties. Individual explanted mesh specimens were placed in a 50 mL Falcon tube containing 25 mL collagenase (type I) solution (1.0 mg/mL) in TESCA buffer (50 mM TES, 2 mM calcium chloride, 10 mM NaN3, pH 7.4, sterile filtered). The tube was placed in a shaker (50 rpm) and incubated at 37° C. overnight (~17 h) to digest and remove tissue attached to the mesh specimen. After the incubation was complete, the specimens were removed from the tubes, residual tissue was manually removed from the explant taking care not to damage the mesh, and the meshes were rinsed with distilled water followed by 70% ethanol. Mesh specimens were blotted dry using a lint-free wipe.

Samples were tested for dimensions, relative stiffness (Taber tester), burst strength and evaluated for surface morphology via SEM. Comparison was made to non-implanted (T0) articles (n=9/group). Polymer degradation was further evaluated by Gel Permeation Chromatography (GPC). The host tissue response and degree of tissue remodeling were evaluated histologically Burst Test, Stiffness & Molecular Weight (Mw) Retention of PBS Mesh The thickness of each sample was measured with a pro-gage thickness tester before testing for burst strength. The burst strength was measured using a universal testing machine (Q test Elite by MTS) fitted with a 1,000 N load cell according to test method ASTM D6797-02, Standard Test Method for Bursting Strength of Fabrics Constant-Rate-of-Extension (CRE) Ball Burst Test. The samples were clamped over the circular opening of the fixture and a ⅜in. probe was lowered through the sample at 305 mm/min until failure. A pre-load setting of 0.05 kg was used to remove slack from the sample and register zero displacement. The load at failure (kgf) was recorded as the bursting strength.

After mechanical testing a portion of the mesh remnant was removed to measure the weight average molecular weight ($M_w$) by Gel Permeation Chromatography (GPC). Mw was measured relative to monodisperse polystyrene standards using a TOSOH HPLC with Refractive Index detector. Samples for GPC were prepared at 1 mg/ml in chloroform, 100 μl of the solutions were injected onto a Polymer Labs, PLgel column (5 micron, mixed C, 300=7.5 mm), and eluted at 1 ml/min in chloroform using a refractive index detector. The test results are summarized in Tables 8 to 12 below.

Tables 8 and 9 show the dimensions (length, width and area of the meshes) of the PBS mesh and GalaFLEX mesh prior to implantation, and after implantation for 4 and 12 weeks. The data shows a surprising difference between the two meshes. Although both are made with the same knit patterns and from similar sized monofilament fibers, the dimensions of the PBS mesh remain essentially constant following implantation whereas the dimensions of the GalaFLEX mesh change over time. It is thus apparent that the PBS mesh is dimensionally stable following implantation, and does not shrink following implantation. The area occupied by the mesh remains constant as shown by the relative area occupied by the PBS mesh in Table 8, as well as the mesh dimensions.

TABLE 8

Dimensional data for PBS Mesh Samples after Implantation Subcutaneously in Rabbit Tissue with In-grown Tissue Intact

| Time (weeks) | Length (mm) | SD (mm) | Width (mm) | SD (mm) | Area | Rel Area (%) |
|---|---|---|---|---|---|---|
| 0 | 38.0 | 0.5 | 38.4 | 0.7 | 1458.8 | 100.0 |
| 4 | 38.6 | 0.9 | 38.9 | 0.8 | 1502.6 | 103.0 |
| 12 | 38.2 | 0.8 | 38.4 | 1.2 | 1466.2 | 100.5 |

TABLE 9

Dimensional data for GalaFLEX Mesh Samples after Implantation Subcutaneously in Rabbit Tissue with In-grown Tissue Intact

| Time (weeks) | Length (mm) | SD (mm) | Width (mm) | SD (mm) | Area | Rel Area (%) |
|---|---|---|---|---|---|---|
| 0 | 38.1 | 0.3 | 38.1 | 0.3 | 1452.5 | 100.0 |
| 4 | 37.1 | 1.1 | 37.4 | 1.3 | 1384.4 | 95.3 |
| 12 | 37.0 | 1.6 | 37.0 | 2.0 | 1369.0 | 94.3 |

Table 11 shows that the burst strength of the PBS mesh decreases over 12 weeks from 22.668 kgf to 16.801 kgf, representing a strength retention of 74.1%. Table 10 shows that tissue in-growth into the PBS mesh results in a lower loss of burst strength when the explant is tested without removal of the in-grown tissue. In this case, the burst strength decreases from 22.668 kgf to only 18.288 kgf, representing a strength retention of 80.7% over the 12-week period. It is apparent from this data, that the PBS mesh can support tissue in-growth, and that this in-growth contributes an additional 80.7%-74.1%=6.6% to the burst strength of the mesh by 12 weeks post-implantation. Table 11 also shows that the stiffness of the PBS mesh (measured in Taber Stiffness Units) remains relatively constant throughout the 12-week implantation period even though the burst strength of the mesh decreases about 25% during this period.

TABLE 10

Mechanical Data for PBS Mesh Samples after Implantation Subcutaneously in Rabbit Tissue with In-grown Tissue Intact

| Time (wks) | Burst Strength (kgf) | Burst Strength SD (kgf) | Strength Retention (%) | Thickness (mm) | Thick. SD (mm) | Taber Stiffness | Taber Stiff. SD | Relative Stiffness |
|---|---|---|---|---|---|---|---|---|
| 0 | 22.668 | 0.887 | 100.0 | 0.683 | 0.024 | 0.262 | 0.116 | 100.0 |
| 4 | 19.827 | 0.699 | 87.5 | 0.716 | 0.058 | 0.261 | 0.094 | 99.5 |
| 12 | 18.288 | 0.970 | 80.7 | 0.762 | 0.072 | 0.202 | 0.083 | 77.0 |

TABLE 11

Mechanical data for PBS Mesh Samples after Implantation Subcutaneously in Rabbit Tissue after Tissue Digestion with Collagenase to Remove In-grown Fibrotic Tissue

| Time (wks) | Burst Strength (kgf) | Burst Strength SD (kgf) | Strength Retention (%) | Thick. (mm) | Thick. SD (mm) | Taber Stiffness | Taber Stiff. SD | Rel. Stiffness |
|---|---|---|---|---|---|---|---|---|
| 0 | 22.668 | 0.887 | 100.0 | 0.683 | 0.024 | 0.262 | 0.116 | 100.0 |
| 4 | 19.480 | 1.831 | 85.9 | 0.677 | 0.027 | 0.262 | 0.101 | 100.1 |
| 12 | 16.801 | 1.086 | 74.1 | 0.698 | 0.008 | 0.284 | 0.140 | 108.4 |

Table 12 shows the reduction in the weight average molecular weight (Mw) of the PBS polymer used to prepare the PBS mesh implant at 4 and 12 weeks compared to the initial Mw. The data demonstrates that the PBS mesh implant degrades in vivo, and that the retention of weight average molecular weight of the polymer is 89.7% at 4 weeks, and 72.5% at 12 weeks. The finding of the good retention of strength of the PBS mesh means that it is suitable for use in procedures requiring prolonged strength retention.

TABLE 12

Weight Average Molecular Weight (Mw) of PBS Mesh Samples after Implantation Subcutaneously in Rabbit Tissue after Tissue Digestion with Collagenase to Remove In-grown Fibrotic Tissue.

| Time (wks) | Mw (kDaltons) | SD (kDaltons) | Mw Retention (%) |
|---|---|---|---|
| 0 | 173 | 0.5 | 100.0 |
| 4 | 155 | 0.5 | 89.7 |
| 12 | 126 | 1.9 | 72.5 |

Biocompatibility and Histological of PBS Mesh

At 4 weeks, gross examination showed that the tissue had completely integrated into the pores of the mesh implants. Microscopically, marked tissue ingrowth into the implant material was noted at all 3 sites and consisted of new fibrous connective tissue, neovascularization, and inflammation extending into the spaces between implant material fibers (i.e. the mesh pores).

The tissue reaction of the PBS Mesh was graded relative to the comparative commercial control, GalaFLEX Mesh. The scores were fairly similar between mesh implant types at 4 weeks, with implant material fibers embedded in a new fibrous connective tissue band, and with macrophages and multinucleated giant cells being the dominant inflammatory cell types at most sites, surrounding and separating the implant material fibers. At 4 weeks, there were overall slightly fewer multinucleated giant cells responding to the PBS material fibers than to the GalaFLEX fibers, and slightly more polymorphonuclear cells. There was also slightly less neovascularization overall at the PBS than P4HB sites.

Figure 2:
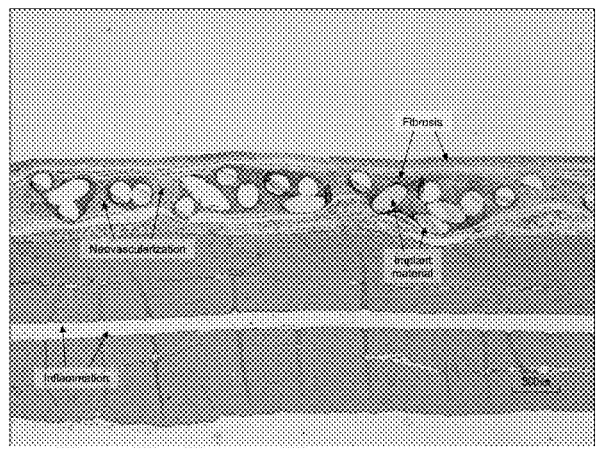
FIG. 2 is an image of a paraffin-embedded tissue slide showing the histology of a PBS mesh after subcutaneous implantation in a rabbit for a 4-week period using an H&E stain at a magnification of 20×.
Figure 3:
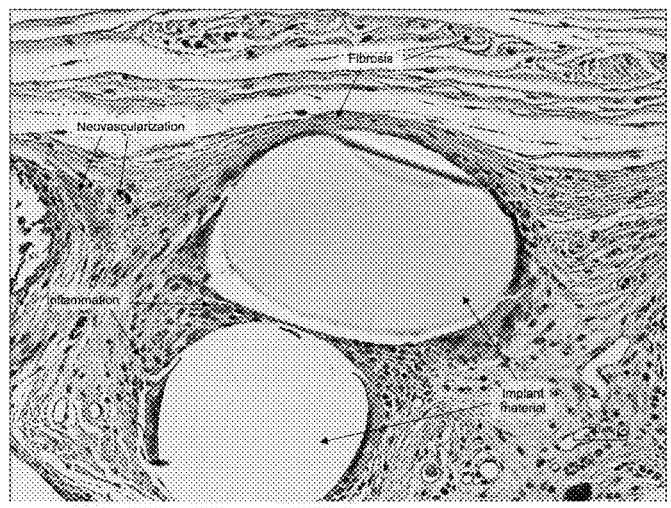
FIG. 3 is an image of a paraffin-embedded tissue slide, showing the histology of a PBS mesh after subcutaneous implantation in a rabbit for a 4-week period using an H&E stain at a magnification of 200×.

PBS implant sites contained implant material, consisting of roughly circular, elliptical, or elongate cross-sections through fibers of clear, refractile, birefringent material arranged in multiple small clusters in a row parallel to the skin surface (see FIGS. 2 and 3). Implant material fibers had a finely granular texture. Implant material fibers were surrounded and separated by the peri-implant tissue, which consisted of a continuous moderately thick to thick band of mostly immature collagen (graded 4), with small foci of mature collagen (graded 1) and with moderate neovascularization. A continuous 1-3 cell-thick layer of macrophages (moderate) and multinucleated giant cells (minimal to mild) lined the surface of implant fibers embedded within the fibrous connective tissue band. The new fibrous connective tissue was infiltrated by variable inflammatory cells, including scattered to small aggregates of macrophages, multinucleated giant cells, polymorphonuclear cells (minimal to moderate), lymphocytes (minimal), and plasma cells (minimal). Minimal necrosis or apoptosis of inflammatory cells was an expected finding at sites of inflammation.

Based on the Irritant Rank Score relative to a comparative control mesh (GalaFLEX mesh), the PBS test article was considered a non-irritant. And the PBS mesh considered to be biocompatible.

Example 16: Determination of the Strength Retention of a PBS Suture Fiber, and its Local Tissue Reaction PBS oriented monofilament fiber samples (0.109±0.004 mm) (USP suture size 6/0) were implanted in the dorsal, subcutaneous tissue of New Zealand White rabbits to evaluate the local tissue reaction and the changes in mechanical properties of the fibers over time in vivo. Three (3) male New Zealand White (NZW) rabbits were implanted with 3 mechanical (9 in.), 1 histological/SEM (9 in.) test articles per animal.

Prior to implantation, the rabbits (weighing at least 3.5 kg at implantation) were anesthetized by an intramuscular injection, followed by maintenance under isoflurane. Following anesthesia, the animals were injected subcutaneously with an analgesic. The surgical sites were prepared for implantation. An incision was made cranially through the skin and a long forcep was tunneled through the subcutaneous tissue and parallel to the spine to exit caudally through a second skin incision. A single suture fiber was grasped by the forceps and pulled back into the tissue. This process was repeated to implant each fiber. Four test PBS suture fibers (3 mechanical samples and 1 histo/SEM sample) and four control monofilament fibers made of poly-4-hydroxybutyrate (TephaFLEX monofilament suture, Tepha, Inc. Lexington, Massachussetts) were implanted on each side of each animal, for a total of 8 specimens per animal. The skin was closed and a bandage was applied. The animals were returned to their respective cages, monitored for recovery from the anesthetic, and then monitored daily for general health.

At 4 weeks, all three rabbits were euthanized. The skin was reflected, the subcutaneous tissues were examined and the area around each implant was dissected free. The implanted sutures were recovered by dissection from the surrounding tissue. The explants were processed for histological, biomechanical and polymer testing. The explanted sutures (n=9) were tested for tensile mechanical properties. The other samples (n=3), were designated for histopathology.

Analysis of the local tissue reaction by histopathology demonstrated that the PBS suture was graded as a non-irritant relative to the comparative poly-4-hydroxybutyrate (TephaFLEX) suture control.

Tensile testing was performed on a Universal Testing Machine operating on the principle of constant rate of elongation of test specimen. The tensile testing machine was equipped with pneumatic fiber grips, using a pre-load setting of 0.05 kg. A gauge length of 138 mm and a strain rate of 300 mm/minute were used. During testing, the location of the break was recorded.

After mechanical testing a portion of the suture remnant was removed to measure the weight average molecular weight ($M_w$) by Gel Permeation Chromatography (GPC). Mw was measured relative to monodisperse polystyrene standards using a TOSOH HPLC with Refractive Index detector as described above for mesh. The test results are summarized in Table 13. The results shown in Table 13 show the PBS monofilament suture retained 92.7% of its initial weight average molecular weight at 4 weeks post-implantation indicating that the suture had begun to degrade in vivo, but could retain substantial strength over a critical wound healing period.

TABLE 13

Mechanical and Weight Average Molecular Weight (Mw) data for PBS suture samples after subcutaneous implantation in rabbits

| Time point (weeks) | Peak Load (kgf) | Std Dev (kgf) | Break Elongation (%) | Strength Retention (%) | Mw (kDa) | Std Dev (kDa) | Mw Retention (%) |
|---|---|---|---|---|---|---|---|
| 0 | 1.771 | 0.034 | 24.063 | 100 | 172 | 1.5 | 100 |
| 4 | 1.749 | 0.044 | 25.694 | 99 | 159 | 0.8 | 92.7 |

Figure 4:
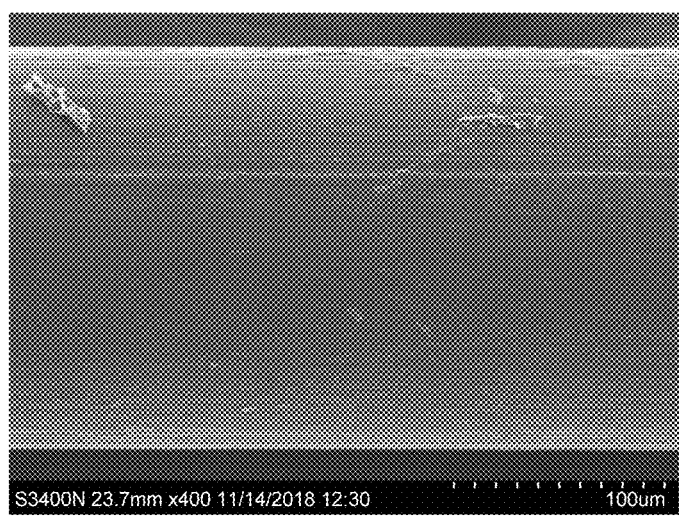
FIG. 4 is a SEM image of an oriented PBS monofilament suture fiber prior to implantation at a 400× magnification showing a smooth surface.

The subcutaneously implanted oriented PBS monofilament suture fiber was analyzed by SEM after it had been implanted for 4 weeks. The SEM image was compared to an unimplanted PBS suture fiber. SEM images were recorded with a 400× magnification. FIG. 4 shows the SEM image of the oriented PBS suture fiber prior to implantation. FIG. 5 shows the SEM image of the oriented PBS suture fiber after subcutaneous implantation for 4 weeks. Surprisingly, there is no evidence of surface erosion of the implanted PBS suture fiber after 4 weeks in vivo. The SEM image in FIG. 5 shows no evidence of surface erosion of the fiber.

Example 17: Preparation of a Poly(butylene succinate) Mesh Suture

A mesh suture was prepared using triaxial braiding from high strength monofilament PBS fibers. Spooled monofilament fibers of succinic acid-1,4-butanediol-malic acid copolyester extruded and oriented as described in Example 2 were unspooled and wound on braider bobbins. The bobbins were then loaded onto Herzog 4, 8, 16 and 24 carrier braiders. Additional spooled monofilament fiber was used to provide axial fiber in the mesh suture. The monofilament fibers were unspooled and threaded through the hollow axles of the horn gears, and all bobbin and axial fiber ends were pulled through the braiding ring to form the fell point. The braiders' bobbins were allowed to move along the braiding track, and the braid helix angle was adjusted to 15 degrees at 1 to 2 Picks Per Inch (PPI). The constructions (number of carriers and axial fibers used to prepare the hollow braids) and properties of the triaxial braided mesh sutures prepared with 100 μm, 150 μm, and 200 μm P4HB monofilament fiber are shown in Tables 14, 15 and 16. The tables show the outside (OD) and inside (ID) diameters of the mesh suture hollow braids. The width and thickness of the hollow braided mesh sutures were measured after the hollow braids had been squashed flat.

TABLE 14

Properties of Triaxial Hollow Braids Prepared with 100 μm PBS Monofilament Fibers

| Braider | | Hollow Triaxial Braid | | | | Tensile |
|---|---|---|---|---|---|---|
| | | Circular | | Flattened | | |
| # Carriers | # Pillar Fibers | OD (mm) | ID (mm) | Width (mm) | Thickness (mm) | Strength (N) |
| 4 | 2 | 0.8 | 0.4 | 1.2 | 0.4 | 47 |
| 8 | 4 | 1.0 | 0.6 | 1.5 | 0.4 | 99 |
| 12 | 6 | 1.3 | 0.9 | 2.0 | 0.4 | 149 |
| 16 | 8 | 1.7 | 1.2 | 2.6 | 0.4 | 200 |
| 24 | 12 | 2.8 | 2.2 | 3.4 | 0.4 | 297 |

TABLE 15

Properties of Triaxial Hollow Braids Prepared with 169 μm PBS Monofilament Fibers

| Braider | | Hollow Triaxial Braid | | | | Tensile |
|---|---|---|---|---|---|---|
| | | Circular | | Flattened | | |
| # Carriers | # Pillar Fibers | OD (mm) | ID (mm) | Width (mm) | Thickness (mm) | Strength (N) |
| 4 | 2 | 1.0 | 0.4 | 1.5 | 0.6 | 97 |
| 8 | 4 | 1.5 | 0.9 | 2.3 | 0.6 | 199 |
| 12 | 6 | 2.5 | 1.9 | 3.9 | 0.6 | 291 |
| 16 | 8 | 3.0 | 2.4 | 4.7 | 0.6 | 389 |
| 24 | 12 | 4.0 | 3.4 | 6.2 | 0.6 | 584 |

TABLE 16

Properties of Triaxial Hollow Braids Prepared with 200 μm PBS Monofilament Fibers

| Braider | | Hollow Triaxial Braid | | | | Tensile |
|---|---|---|---|---|---|---|
| | | Circular | | Flattened | | |
| # Carriers | # Pillar Fibers | OD (mm) | ID (mm) | Width (mm) | Thickness (mm) | Strength (N) |
| 4 | 2 | 1.1 | 0.3 | 1.7 | 0.8 | 129 |
| 8 | 4 | 1.6 | 0.8 | 2.5 | 0.8 | 259 |
| 12 | 6 | 2.5 | 1.7 | 3.9 | 0.8 | 389 |
| 16 | 8 | 3.5 | 2.7 | 5.4 | 0.8 | 518 |
| 24 | 12 | 5.0 | 4.1 | 7.8 | 0.8 | 778 |

Example 18: 3D Printing of a PBS-Malic Acid Copolymer Implant by Melt Extrusion Deposition (MED)

A PBS-malic acid copolymer implant was printed by MED using equipment having a horizontal extruder feeding into a vertical extruder fitted with a vertical plunger, and a movable stage. The extruder hopper was charged with PBS-malic acid copolymer pellets (160 kDa, by GPC relative to polystyrene standards) with a diameter of about 2-3 mm and moisture content of about 300 ppm. The pellets were kept dry in the hopper using a purge of air dried through a silica bed. The temperature profile of the horizontal extruder was set to about 30° C. in the build chamber; with the temperatures for the transition zone 1, zone 2; and zone 3 (extrusion zone) for various trials as shown in Table 17. The residence time of the polymer in the MED horizontal extruder was approximately 22 min/cm³. The diameter of the nozzle orifice of the vertical extruder was 0.2 mm and the drop printing frequency was about 50 drops/sec at the edge of the printed construct and about 240 drops/sec for the in-fill. Under these conditions, it was possible to print implants made from PBS-malic acid copolymer with good print quality. The weight average molecular weight, Mw, of the printed implants was measured by GPC and is also shown in Table 17. The Mw and polydispersity (PDI) were found to vary with the extrusion conditions used. As is evident from Table 17, the weight average molecular weight of the printed implants increased as the temperature was raised from 180° C. to 220° C.

TABLE 17

Properties of Implants made from PBS and Copolymers thereof Prepared Under Different Thermal Conditions by MED 3D Printing

| Description | Zone 1 | Zone 2 | Zone 3 | Mw (kDa) | PDI |
|---|---|---|---|---|---|
| Lot #170065 (PBS-Malic Acid Copolymer Pellets) | | | | 160.4 | 2.97 |
| PBS Tn180 | 100 | 130 | 180 | 164.5 | 2.88 |
| PBS Tn190 | 110 | 140 | 190 | 170.0 | 2.96 |
| PBS Tn200 | 120 | 150 | 200 | 180.8 | 3.00 |
| PBS Tn210 | 130 | 160 | 210 | 190.7 | 3.09 |
| PBS Tn220 | 140 | 170 | 220 | 209.4 | 3.26 |
| PBS Tn230 | 160 | 190 | 230 | 192.1 | 3.27 |

We claim:

1. An implant comprising fibers of a polymeric composition, wherein the polymeric composition comprises one or more 1,4-butanediol units and one or more succinic acid units, wherein the fibers comprise a monofilament fiber, a multifilament fiber, or a combination thereof, wherein the monofilament fiber has a tensile strength of 400 to 2,000 MPa and the multifilament fiber has a tenacity of greater than 4 grams/denier and less than 14 grams/denier, and
wherein the implant comprises a mesh, a film, a nonwoven construct, a molded object, a patch, a tube, a laminate, or a pultruded profile.

2. The implant of claim 1, wherein the fibers are braided or barbed.

3. The implant of claim 1, wherein the implant comprises the mesh, and wherein the mesh is knitted or woven from the monofilament fibers and/or the multifilament fibers.

4. The implant of claim 1, wherein the fibers are mono-axially or biaxially oriented.

5. The implant of claim 1, wherein the implant is porous.

6. The implant of claim 2, wherein a tensile strength of the fibers is between 500 MPa and 1,200 MPa.

7. The implant of claim 1, wherein the fibers have a Young's Modulus of at least 600 MPa, but less than 3 GPa.

8. The implant of claim 1, wherein the mesh has a burst strength between 1 kgf or a Taber stiffness between 0.01 and 10 Taber stiffness units.

9. The implant of claim 1 wherein: (a) there is no pitting of a surface of the implant during degradation in vivo, under physiological conditions, for a period of 4 weeks or (b) when implanted under physiological conditions, in vivo for a period of 4 weeks, dimensions of the implant do not shrink more than 5% of their initial values.

10. The implant of claim 1, wherein the polymeric composition further comprises (a) one or more of the following: a second diacid unit, a second diol unit, 1,3-propanediol, ethylene glycol, 1,5-pentanediol, glutaric acid, adipic acid, terephthalic acid, malonic acid, and oxalic acid; (b) one or more of the following: a branching agent, a cross-linking agent, a chain extender agent, and a reactive blending agent; or (c) a hydroxycarboxylic acid unit.

11. The implant of claim 10, wherein the branching agent, cross-linking agent, or chain extender unit is selected from one or more of the following: malic acid, maleic acid, fumaric acid, trimethylol propane, trimesic acid, citric acid, glycerol propoxylate, and tartaric acid.

12. The implant of claim 1, wherein the polymeric composition comprises succinic acid-1,4-butanediol-malic acid copolyester, succinic acid-1,4-butanediol-citric acid copolyester, succinic acid-1,4-butanediol-tartaric acid copolyester, succinic acid-1,4-butanediol-malic acid copolyester further comprising citric acid, tartaric acid, or a combination thereof, succinic acid-adipic acid-1,4-butanediol-malic acid copolyester, succinic acid-adipic acid-1,4-butanediol-citric acid copolyester, succinic acid-adipic acid-1,4-butanediol-tartaric acid copolyester, or succinic acid-adipic acid-1,4-butanediol-malic acid copolyester further comprising citric acid, tartaric acid, or combinations thereof.

13. The implant of claim 1, wherein the implant further comprises a plasticizer, nucleant, coating, dye, medical marker, bioactive agent, therapeutic agent, diagnostic agent, prophylactic agent, contrast agent, radiopaque marker, radioactive substance, anti-adhesion agent, hyaluronic acid, antibiotic, rifampin, minocycline, collagen, hydroxyapatite, or an absorbable polymer comprising one or more of the following monomers: glycolic acid, lactic acid, trimethylene carbonate, p-dioxanone, ε-caprolactone, 4-hydroxybutyric acid, and 3-hydroxybutyric acid.

14. The implant of claim 1, wherein the polymeric composition: (i) excludes urethane bonds, (ii) is not prepared with a diisocyanate, (iii) comprises 1-500 ppm of one or more, or all, of the following: silicon, titanium, and zinc, (iv) excludes tin or (v) is not a blend of two or more polymers.

15. The implant of claim 1, wherein the polymeric composition has a melt temperature between 100° C. and 150° C.

16. The implant of claim 1, wherein the implant is selected from the group consisting of: a suture, a barbed monofilament suture, a braided suture, a mesh suture, a wound closure device, a patch, a wound healing device, a wound dressing, a burn dressing, an ulcer dressing, a skin substitute, a hemostat, a tracheal reconstruction device, an organ salvage device, a dural patch or substitute, a nerve regeneration or repair device, a hernia repair device, a hernia mesh, a hernia plug, an inguinal hernia plug, a device for temporary wound or tissue support, a tissue engineering scaffold, a guided tissue repair/regeneration device, an anti-adhesion membrane or barrier, a tissue separation membrane, a retention membrane, a sling, a device for pelvic floor reconstruction, a device for treatment of pelvic organ prolapse, an urethral suspension device, a device for treatment of urinary incontinence, a device for treatment of stress urinary incontinence, a bladder repair device, a bulking or filling device, a bone marrow scaffold, a bone plate, a fixation device for an implant, a ligament repair device or augmentation device, an anterior cruciate ligament repair device, a tendon repair device or augmentation device, a rotator cuff repair device, a meniscus repair or regeneration device, an articular cartilage repair device, an osteochondral repair device, a spinal fusion device, a cardiovascular patch, a catheter balloon, a vascular closure device, an intracardiac septal defect repair device, an atrial septal defect repair device a patent foramen ovale closure device, a left atrial appendage closure device, a pericardial patch, a vein valve, a heart valve, a vascular graft, a myocardial regeneration device, a periodontal mesh, a guided tissue regeneration membrane for periodontal tissue, an ocular cell implant, an imaging device, a cochlear implant, an anastomosis device, a cell seeded device, a cell encapsulation device, a controlled release device, a drug delivery device, a plastic surgery device, a mastopexy device, a breast reconstruction device, a breast augmentation device, a breast reduction device, a breast implant, a device for removing, reshaping and reorienting breast tissue, a device for breast reconstruction following mastectomy with or without breast implants, a facial reconstructive device, a forehead lift device, a brow lift device, an eyelid lift device, a rhytidectomy device, a thread lift device, a device to lift and support sagging areas of the face and brow, a rhinoplasty device, a device for malar augmentation, an otoplasty device, a neck lift device, a mentoplasty device, a buttock lift device, a cosmetic repair device, and a device for facial scar revision.

17. The implant of claim 16, wherein the implant is a braided suture comprising a multifilament fiber, wherein the breaking strength of the braided suture is from 40_N to 270_N.

18. The implant of claim 1, wherein the implant contains less than 20 endotoxin units as determined by the limulus amebocyte lysate (LAL) assay.

19. The implant of claim 1 wherein the fibers are multi-filament fibers.

20. The implant of claim 10, wherein the polymeric composition comprises the hydroxycarboxylic acid unit, and wherein the hydroxycarboxylic acid unit has two carboxyl groups and one hydroxyl group, two hydroxyl groups and one carboxyl group, three carboxyl groups and one hydroxyl group, or two hydroxyl groups and two carboxyl groups.

21. The implant of claim 1, wherein the polymeric composition excludes urethane bonds and is not prepared with a diisocyanate.

22. The implant of claim 1, wherein the fibers have an elongation to break of between 15% and 50%.

23. The implant of claim 1, wherein the fibers have an elongation to break of 10% to 50% and either or both of a tensile strength between 400 MPa and 1200 MPa and a Young's Modulus between 600 MPa and 3.0 GPa.

24. The implant of claim 1, wherein the fibers have been subjected to one or more stages of drawing, each of the stages with an orientation ratio of at least 1.0 at a temperature of 70-75° C.

25. The implant of claim 24, wherein the fibers have been further subjected to one or more additional stages of drawing, each of the additional stages with an orientation ratio of at least 3.5 at a temperature of 50-70° C.

26. The implant of claim 25, wherein the fibers have been subjected to one or more stages of drawing, each of the stages with an orientation ratio, wherein the sum of the orientation ratios of all of the stages of drawing is over 6.0.

27. The implant of claim 24, wherein the fibers have been further subjected to one or more stages of drawing, each of the stages with an orientation ratio of at least 2.0 at a temperature of 65-75° C.

28. A method for making the implant of claim 1, comprising:
providing the polymeric composition and forming or incorporating the polymeric composition into the implant by one or more processes comprising: casting, solvent casting, solution spinning, solution bonding of fibers, melt processing, extrusion, melt extrusion, melt spinning, fiber spinning, orientation, relaxation, annealing, injection molding, compression molding, lamination, dry spinning, knitting, weaving, crocheting, melt-blowing, film formation, film blowing, film casting, membrane forming, electrospinning, thermoforming, pultrusion, centrifugal spinning, molding, tube extrusion, spunbonding, nonwoven fabrication, entangling of staple fibers, fiber knitting, weaving and crocheting, mesh fabrication, coating, dip coating, laser cutting, barbing, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, or printing using a binding solution and granules of powder.

29. The method of claim 28, wherein the implant is selected from the group consisting of: a suture, a barbed suture, a monofilament suture, a braided suture, a mesh suture, a wound closure device, a patch, a wound healing device, a wound dressing, a burn dressing, an ulcer dressing, a skin substitute, a hemostat, a tracheal reconstruction device, an organ salvage device, a dural patch or substitute, a nerve regeneration or repair device, a hernia repair device, a hernia mesh, a hernia plug, an inguinal hernia plug, a device for temporary wound or tissue support, a tissue engineering scaffold, a guided tissue repair/regeneration device, an anti-adhesion membrane or barrier, a tissue separation membrane, a retention membrane, a sling, device for pelvic floor reconstruction, a device for treatment of pelvic organ prolapse, an urethral suspension device, a device for treatment of urinary incontinence, a device for treatment of stress urinary incontinence, a bladder repair device, a bulking or filling device, a bone marrow scaffold, a bone plate, a fixation device for an implant, a ligament repair device or augmentation device, an anterior cruciate ligament repair device, a tendon repair device or augmentation device, a rotator cuff repair device, a meniscus repair or regeneration device, an articular cartilage repair device, an osteochondral repair device, a spinal fusion device, a cardiovascular patch, a catheter balloon, a vascular closure device, an intracardiac septal defect repair device, an atrial septal defect repair device, a patent foramen ovale closure device, a left atrial appendage closure device, a pericardial patch, a vein valve, a heart valve, a vascular graft, a myocardial regeneration device, a periodontal mesh, a guided tissue regeneration membrane for periodontal tissue, an ocular cell implant, a imaging device, a cochlear implant, an anastomosis device, a cell seeded device, a cell encapsulation device, a controlled release device, a drug delivery device, a plastic surgery device, a mastopexy device, a breast reconstruction device, a breast augmentation device, a breast reduction device, a breast implant, a device for removing, reshaping and reorienting breast tissue, a device for breast reconstruction following mastectomy with or without breast implants, a facial reconstructive device, a forehead lift device, a brow lift device, an eyelid lift device, a rhytidectomy device, a thread lift device, a device to lift and support sagging areas of the face and brow, a rhinoplasty device, a device for malar augmentation, an otoplasty device, a neck lift device, a mentoplasty device, a buttock lift device, a cosmetic repair device, and a device for facial scar revision.

30. A method of enhancing the healing of a wound, injury, or defect in a site of a patient, or repairing or regenerating tissue in a site of a patient, comprising administering at the site the implant of claim 1.

\* \* \* \* \*

UNITED STATES PATENT AND TRADEMARK OFFICE
CERTIFICATE OF CORRECTION

PATENT NO. : 11,878,087 B2
APPLICATION NO. : 16/290727
DATED : January 23, 2024
INVENTOR(S) : Simon F. Williams et al.

It is certified that error appears in the above-identified patent and that said Letters Patent is hereby corrected as shown below:

In the Claims

Column 52, Claim 8, Line 22, replace "between 1 kgf or a Taber stiffness between 0.01 and 10 Taber stiffness units." with --between 1 kgf and 100 kgf or a Taber stiffness between 0.01 and 10 Taber stiffness units.--

Signed and Sealed this
Second Day of April, 2024

Katherine Kelly Vidal
*Director of the United States Patent and Trademark Office*